United States Patent
Wang

(10) Patent No.: US 12,198,795 B2
(45) Date of Patent: Jan. 14, 2025

(54) CALCULATION METHOD OF FOOD VOLUME AND FOOD CALORIES, ELECTRONIC APPARATUS, ELECTRONIC DEVICE AND STORAGE MEDIUM

(71) Applicant: BOE Technology Group Co., Ltd., Beijing (CN)

(72) Inventor: Sifan Wang, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 654 days.

(21) Appl. No.: 17/426,894

(22) PCT Filed: Oct. 15, 2020

(86) PCT No.: PCT/CN2020/121175
§ 371 (c)(1),
(2) Date: Jul. 29, 2021

(87) PCT Pub. No.: WO2022/077348
PCT Pub. Date: Apr. 21, 2022

(65) Prior Publication Data
US 2022/0319665 A1    Oct. 6, 2022

(51) Int. Cl.
*G16H 20/60*    (2018.01)
*G06T 7/62*    (2017.01)

(52) U.S. Cl.
CPC .............. *G16H 20/60* (2018.01); *G06T 7/62* (2017.01); *G06T 2207/30128* (2013.01)

(58) Field of Classification Search
CPC .......... G16H 20/60; G16H 40/63; G06T 7/62; G06T 2207/30128; G06T 2207/10012;
(Continued)

(56) References Cited

U.S. PATENT DOCUMENTS 9,571,818 B2 *   2/2017  Pulli ..................... H04N 13/254
11,138,901 B1 *  10/2021 Angel .................... G06V 20/00
(Continued)

FOREIGN PATENT DOCUMENTS

| AU | 2018100707 A4 | 7/2018 |
| CN | 103646408 A | 3/2014 |

(Continued)

OTHER PUBLICATIONS

Dehais et al. "Two-view 3D reconstruction for food volume estimation." IEEE transactions on multimedia 19.5 (2016): 1090-1099. (Year: 2016).*

(Continued)

*Primary Examiner* — Edward F Urban
*Assistant Examiner* — Benedict E Lee
(74) *Attorney, Agent, or Firm* — Banner & Witcoff, Ltd.

(57) ABSTRACT

A calculation method of food volume, a calculation method of food calories, an electronic apparatus, an electronic device and a computer-readable storage medium are provided. The calculation method of food volume includes: acquiring actual size information of a stereo reference object; acquiring a reference image corresponding to the stereo reference object and a food image corresponding to food to be estimated; and acquiring volume information of the food to be estimated, according to the actual size information of the stereo reference object, reference region size information acquired based on the reference image, and food region size information acquired based on the food image. The calculation method of food volume reduces the complexity of operation and enhances the flexibility of application.

18 Claims, 11 Drawing Sheets

(58) Field of Classification Search
CPC . G06T 2207/10024; G06T 2207/20081; G06T 2207/20084
See application file for complete search history.

(56) References Cited

U.S. PATENT DOCUMENTS

| | | | |
|---|---|---|---|
| 11,450,013 B2* | 9/2022 | Yuan | G06T 1/00 |
| 11,562,817 B2* | 1/2023 | Kim | G16H 40/67 |
| 2011/0077471 A1 | 3/2011 | King | |
| 2014/0349256 A1 | 11/2014 | Connor | |
| 2015/0030247 A1* | 1/2015 | Shu | G06T 5/77 |
| | | | 382/167 |
| 2020/0281464 A1* | 9/2020 | Tokuda | A61B 3/1225 |
| 2021/0390673 A1* | 12/2021 | Ban | G06T 7/194 |
| 2021/0398305 A1* | 12/2021 | Lee | G06T 7/593 |
| 2022/0007689 A1* | 1/2022 | Baldwin | G06T 7/73 |
| 2022/0254175 A1* | 8/2022 | Heinrich | G16H 30/40 |

FOREIGN PATENT DOCUMENTS

| | | |
|---|---|---|
| CN | 104778374 A | 7/2015 |
| CN | 104809430 A | 7/2015 |
| CN | 105865326 A | 8/2016 |
| CN | 107341439 A | 11/2017 |
| CN | 107958696 A | 4/2018 |
| CN | 108256421 A | 7/2018 |
| CN | 108509853 A | 9/2018 |
| CN | 108564034 A | 9/2018 |
| CN | 108573503 A | 9/2018 |
| CN | 109243579 A | 1/2019 |
| CN | 109509535 A | 3/2019 |
| CN | 109598206 A | 4/2019 |
| CN | 109614922 A | 4/2019 |
| CN | 111127545 A | 5/2020 |
| GB | 2561556 A | 10/2018 |

OTHER PUBLICATIONS

Subhi et al. "Food volume estimation based on stereo image analysis." IEEE Instrumentation & Measurement Magazine 21.6 (2018): 36-43. (Year: 2018).*

* cited by examiner

CALCULATION METHOD OF FOOD VOLUME AND FOOD CALORIES, ELECTRONIC APPARATUS, ELECTRONIC DEVICE AND STORAGE MEDIUM

The application is a U.S. National Phase Entry of International Application No. PCT/CN2020/121175 filed on Oct. 15, 2020, designating the United States of America. The present application claims priority to and the benefit of the above-identified applications and the above-identified applications are incorporated by reference herein in their entirety.

TECHNICAL FIELD

At least one embodiment of the present disclosure relates to a calculation method of food volume, a calculation method of food calories, an electronic apparatus, an electronic device and a computer-readable storage medium.

BACKGROUND

With the development of economy, the dietary level of urban and rural residents has been significantly improved, which leads to obesity, hypertension and hyperlipidemia in a large number of people and has a negative impact on their health; In addition, teenagers, pregnant women, dieters and ordinary people all need to manage their daily diet in order to keep healthy. For this kind of population, it is necessary to estimate the calories intake of food. The key of food calories estimation is food volume estimation.

SUMMARY

An embodiment of the present disclosure provides a calculation method of food volume, comprising: acquiring actual size information of a stereo reference object; acquiring a reference image corresponding to the stereo reference object and a food image corresponding to food to be estimated; and acquiring volume information of the food to be estimated, according to the actual size information of the stereo reference object, reference region size information acquired based on the reference image, and food region size information acquired based on the food image.

For example, in the method provided by at least an embodiment of the present disclosure, acquiring the reference image corresponding to the stereo reference object and the food image corresponding to food to be estimated, comprises: acquiring one reference image corresponding to the stereo reference object and one food image corresponding to the food to be estimated in a same image-shooting mode, wherein the volume information of the food to be estimated is acquired, according to the actual size information of the stereo reference object, the reference region size information acquired based on the one reference image, and the food region size information acquired based on the one food image; or acquiring a plurality of reference images and a plurality of food images which are correspondingly acquired in pair corresponding to the stereo reference object and the food to be estimated in a plurality of image-shooting modes, wherein the volume information of the food to be estimated is acquired, according to the actual size information of the stereo reference object, the reference region size information acquired based on the plurality of reference images, and the food region size information acquired based on the plurality of food images, wherein the same image-shooting mode or each of the plurality of image-shooting modes at least comprises a shooting distance and a shooting direction.

For example, in the method provided by at least an embodiment of the present disclosure, the plurality of image-shooting modes comprise a first image-shooting mode and a second image-shooting mode, a shooting direction of the first image-shooting mode and a shooting direction of the second image-shooting mode cross each other; the plurality of reference images comprise a first reference image obtained in the first image-shooting mode and a second reference image obtained in the second image-shooting mode; the plurality of food images comprise a first food image obtained in the first image-shooting mode and a second food image obtained in the second image-shooting mode.

For example, in the method provided by at least an embodiment of the present disclosure, each of the plurality of image-shooting modes further comprises a bearing surface on which the stereo reference object or the food to be estimated is placed, the shooting direction of the first image-shooting mode and the shooting direction of the second image-shooting mode are perpendicular to each other, and the shooting direction of the first image-shooting mode is perpendicular to the bearing surface of the first image-shooting mode, and the shooting direction of the second image-shooting mode is parallel to the bearing surface of the second image-shooting mode.

For example, in the method provided by at least an embodiment of the present disclosure, the reference image and the food image acquired in pair in the same image-shooting mode are a pair of images corresponding to each other, or the reference image and the food image acquired in pair in the same image-shooting mode belong to a same image.

For example, in the method provided by at least an embodiment of the present disclosure, acquiring actual size information of a stereo reference object, comprises: acquiring a plurality of stereo reference images in which the stereo reference object is juxtaposed with a first reference object with a reference size that is acquirable, acquiring the actual size information of the stereo reference object, according to the plurality of stereo reference images and the reference size.

For example, in the method provided by at least an embodiment of the present disclosure, acquiring the actual size information of the stereo reference object, according to the plurality of stereo reference images and the reference size, comprises: for each of the plurality of stereo reference images: obtaining a count of first pixels corresponding to the reference size in the stereo reference image, obtaining a count of second pixels in at least one dimension of the stereo reference object in the stereo reference image, obtaining at least one calculated size in the at least one dimension of the stereo reference object in the stereo reference image, according to the count of the first pixels and the count of the second pixels; and acquiring the actual size information of the stereo reference object based on a plurality of calculated sizes acquired from the plurality of stereo reference images.

For example, in the method provided by at least an embodiment of the present disclosure, acquiring actual size information of the stereo reference object, comprises: acquiring a stereo reference image in which the stereo reference object is placed on one side of a second reference object with a reference area that is acquirable; and acquiring the actual size information of the stereo reference object, according to the stereo reference image and the reference area, wherein the stereo reference image comprises information for calculating the reference area of the second reference object.

For example, in the method provided by at least an embodiment of the present disclosure, acquiring the actual size information of the stereo reference object according to the stereo reference image and the reference area, comprises: acquiring a pixel area of the second reference object in the stereo reference image; obtaining a first mapping ratio based on the pixel area of the second reference object and the reference area; acquiring a pixel area of a region occupied by the stereo reference object in the stereo reference image; acquiring a volume of the stereo reference object according to the first mapping ratio and the pixel area of the region occupied by the stereo reference object, to obtain the actual size information of the stereo reference object.

For example, in the method provided by at least an embodiment of the present disclosure, pixel values of pixels corresponding to the second reference object in the stereo reference image are within a first value range, acquiring the pixel area of a region occupied by the stereo reference object in the stereo reference image, comprises: taking pixels in the stereo reference image whose pixel values do not meet the first value range as a region occupied by the stereo reference object, to obtain the pixel area of the region occupied by the stereo reference object; or, obtaining the pixel area of the region occupied by the stereo reference object, according to a region occupied by the stereo reference object acquired through a deep learning model.

For example, in the method provided by at least an embodiment of the present disclosure, acquiring the pixel area of the second reference object in the stereo reference image, comprises: acquiring a minimum bounding rectangle of the second reference object in the stereo reference image and a pixel area of the minimum bounding rectangle, and taking the pixel area of the minimum bounding rectangle as the pixel area of the second reference object, wherein pixel values of pixels corresponding to the second reference object in the stereo reference image are within a first value range, and the minimum bounding rectangle of the second reference object is obtained according to positions of the pixels whose pixel values are within the first value range; and acquiring the pixel area of the region occupied by the stereo reference object in the stereo reference image, comprises: taking pixels in the minimum bounding rectangle whose pixel values do not meet the first value range as the region occupied by the stereo reference object, to obtain the pixel area of the region occupied by the stereo reference object.

For example, in the method provided by at least an embodiment of the present disclosure, the second reference object is a piece of monochrome paper with a standard size.

For example, in the method provided by at least an embodiment of the present disclosure, the stereo reference object comprises a hand in a fisting state and is processed in a spherical manner, acquiring the pixel area of the region occupied by the stereo reference object in the stereo reference image, comprises: in response to that a wrist part of the hand in the stereo reference image is not at an edge of the second reference object, acquiring a fist image according to a hand detection model, extracting a fist region of the fist image, and acquiring a pixel area of the fist region as the pixel area of the region occupied by the stereo reference object; and in response to that the wrist part of the hand in the stereo reference image is at the edge of the second reference object, taking pixels in the stereo reference image whose pixel values do not meet the first value range as a fist region, and obtaining the pixel area of the fist region as the pixel area of the region occupied by the stereo reference.

For example, in the method provided by at least an embodiment of the present disclosure, acquiring the plurality of reference images and the plurality of food images which are correspondingly acquired in pair according to the stereo reference object and the food to be estimated in a plurality of image-shooting modes, comprises: continuously shooting a plurality of images where the food to be estimated and the stereo reference object are simultaneously located on a same bearing surface, and extracting a plurality of key images from the plurality of images, to obtain the plurality of reference images and the plurality of food images, wherein each of the plurality of key images comprises a corresponding pair of reference image and food image.

For example, in the method provided by at least an embodiment of the present disclosure, continuously shooting the plurality of images where the food to be estimated and the stereo reference object are simultaneously located on the same bearing surface, extracting the plurality of key images from the plurality of images, comprises: for each image of the plurality of images, extracting a to-be-estimated food region occupied by the food to be estimated, and obtaining a pixel area of the to-be-estimated food region corresponding to each image; according to the pixel area of the to-be-estimated food region corresponding to each image, extracting an image in which a relative change of the pixel area of the to-be-estimated food region is larger than a preset threshold as one of the plurality of key images from the plurality of the images, wherein the plurality of key images at least comprises a first key image and a second key image, the first key image comprises the first food image and the first reference image, and the second key image comprises the second food image and the second reference image.

For example, in the method provided by at least an embodiment of the present disclosure, acquiring the volume information of the food to be estimated, according to the actual size information of the stereo reference object, the reference region size information acquired based on the plurality of reference images, and the food region size information acquired based on the plurality of food images, comprises: for each reference image of the plurality of reference images, acquiring a pixel area of a region occupied by the stereo reference object in the reference image, to obtain the reference region size information of the stereo reference object; acquiring a second mapping ratio, according to the reference region size information of the stereo reference object and the actual size information of the stereo reference object; extracting the to-be-estimated food region occupied by the food to be estimated in the first food image, to obtain the food region size information; acquiring food size information according to the food region size information and the second mapping ratio; extracting to-be-estimated food regions occupied by the food to be estimated in the plurality of food images, respectively, and determining a container shape of the food to be estimated according to the to-be-estimated food regions; and acquiring the volume information of the food to be estimated according to the container shape of the food to be estimated and the food size information.

For example, in the method provided by at least an embodiment of the present disclosure, acquiring the volume information of the food to be estimated, according to the actual size information of the stereo reference object, the reference region size information, and the food region size information, further comprises: extracting the to-be-estimated food region occupied by the food to be estimated in the second food image, and determining a height value of the food to be estimated according to the to-be-estimated food region and the second mapping ratio; and acquiring the volume information of the food to be estimated according to the container shape of the food to be estimated, the height value of the food to be estimated, and the food size information.

For example, in the method provided by at least an embodiment of the present disclosure, determining the height value of the food to be estimated according to the to-be-estimated food region and the second mapping ratio, comprises: acquiring a count of pixels corresponding to each column of pixels in the to-be-estimated food region; determining a height component of the food to be estimated according to the count of pixels corresponding to each column of pixels; and determining the height value of the food to be estimated according to the height component and the second mapping ratio.

For example, in the method provided by at least an embodiment of the present disclosure, acquiring the pixel area of the region occupied by the stereo reference object in each of the plurality of reference images, to obtain the reference region size information of the stereo reference object, comprises: for each reference image of the plurality of reference images, extracting a region occupied by the stereo reference object from the reference image, and acquiring the pixel area of the region occupied by the stereo reference object; calculating an average value of all acquired pixel areas of the regions occupied by the stereo reference object in the plurality of reference images, to obtain the reference region size information of the stereo reference object.

For example, in the method provided by at least an embodiment of the present disclosure, the stereo reference object comprises a hand in a fisting state, acquiring the pixel area of the region occupied by the stereo reference object in each of the plurality of reference images, to obtain reference region size information of the stereo reference object, comprises: for each of the plurality of reference images, acquiring a fist image according to a hand detection model, extracting a fist region of the fist image, and acquiring a pixel area of the fist region; and calculating an average value of all acquired pixel areas of the fist regions in the plurality of reference images, to obtain the reference region size information of the stereo reference object.

For example, in the method provided by at least an embodiment of the present disclosure, extracting to-be-estimated food regions occupied by the food to be estimated in the plurality of food images, respectively, and determining the container shape of the food to be estimated according to the to-be-estimated food regions, comprises: extracting a food image, which is in a same corresponding direction as a q-th standard container in a standard container set, from the plurality of food images, to obtain at least one to-be-estimated container image corresponding to the q-th standard container, and for each of the at least one to-be-estimated container image, extracting a to-be-estimated food region occupied by the food to be estimated, respectively; calculating a Euclidean distance between the to-be-estimated food region of the to-be-estimated container image and a shape edge of the q-th standard container in a corresponding direction, to obtain at least one Euclidean distance value; summing the Euclidean distance values corresponding to all directions of the q-th standard container overlaying preset weight values corresponding to all the directions, to obtain the Euclidean distance sum value corresponding to the q-th standard container; detecting a minimum Euclidean distance sum value in a Euclidean distance sum value set corresponding to the standard container set, and taking a standard container corresponding to the minimum Euclidean distance sum value as the container shape of the food to be estimated, wherein q is a positive integer.

For example, in the method provided by at least an embodiment of the present disclosure, the food to be estimated is placed in a container, a shape of the container is known and acquirable, or the shape of the container is determined according to the one food image, acquiring the volume information of the food to be estimated, according to the actual size information of the stereo reference object, the reference region size information acquired based on the one reference image, and the food region size information acquired based on the one food image, comprises: acquiring a pixel area of a region occupied by the stereo reference object in the one reference image, to obtain the reference region size information of the stereo reference object; obtaining a second mapping ratio according to the reference region size information of the stereo reference object and the actual size information of the stereo reference object; extracting a to-be-estimated food region occupied by the food to be estimated in the one food image, to obtain the food region size information; obtaining food size information according to the food region size information and the second mapping ratio; and obtaining the volume information of the food to be estimated according to the shape of the container and the food size information.

For example, in the method provided by at least an embodiment of the present disclosure, determining the shape of the container, comprises: acquiring a standard container recognition model, and determining the container shape of the food to be estimated according to the plurality of food images and the standard container recognition model; or acquiring a standard container recognition model, and determining the container shape of the food to be estimated according to the one food image and the standard container recognition model.

For example, in the method provided by at least an embodiment of the present disclosure, for an image to be processed including the food to be estimated, extracting the to-be-estimated food region occupied by the food to be estimated, comprises: dividing the image to be processed into a plurality of region sets, and performing similarity calculation on each region set of the plurality of region sets, to obtain a similarity value of each region set; merging region sets with similarity values meeting a preset threshold to obtain a plurality of merged regions; taking a closed region out of the plurality of merged regions with a largest pixel area as the to-be-estimated food region of the image to be processed, wherein the similarity calculation comprises one or more combinations of color similarity calculation, texture similarity calculation, size similarity calculation and overlap similarity calculation.

For example, in the method provided by at least an embodiment of the present disclosure, for an image to be processed including the food to be estimated, extracting the to-be-estimated food region occupied by the food to be estimated, comprises: performing edge recognition on the image to be processed based on a depth convolution network model, to obtain the to-be-estimated food region of the food to be estimated in the image to be processed.

Another embodiment of the present disclosure provides a calculation method of food calories, comprising: acquiring a type of food to be estimated; acquiring volume information of the food to be estimated according to the calculation method of food volume according to any one of the embodiments; determining a density of the food to be estimated according to the type of the food to be estimated, and obtaining a weight of the food to be estimated based on the density and the volume information of the food to be estimated; determining a heat density of the food to be estimated according to the type of the food to be estimated, and obtaining calories of the food to be estimated based on the heat density and the weight of the food to be estimated.

Another embodiment of the present disclosure provides an electronic apparatus, comprising: a food volume calculation unit, configured to perform the calculation method of food volume according to any one of the above embodiments, to obtain the volume information of the food to be estimated.

For example, the electronic apparatus provided by at least an embodiment of the present disclosure further comprises: a food calories calculation unit, configured to: acquire a type of food to be estimated, determine a density of the food to be estimated according to the type of the food to be estimated, and obtaining a weight of the food to be estimated based on the density and the volume information of the food to be estimated, and determine a heat density of the food to be estimated according to the type of the food to be estimated, and obtaining calories of the food to be estimated based on the heat density and the weight of the food to be estimated.

For example, the electronic apparatus provided by at least an embodiment of the present disclosure further comprises: an image acquisition unit, configured to acquire a reference image corresponding to the stereo reference object and a food image corresponding to the food to be estimated; and an output unit, configured to display or output the volume information and/or the calories of the food to be estimated.

Another embodiment of the present disclosure provides an electronic device, comprising: a storage, configured to non-instantaneously store computer executable instructions, a processor, configured to executed the computer executable instructions; when the computer executable instructions are executed by the processor, the calculation method of food volume according to any one of above embodiments or the calculation method of food calories according to the above embodiment is achieved.

Another embodiment of the present disclosure provides a storage medium, on which computer executable instructions are stored, wherein when the computer executable instructions are executed by a processor, the calculation method of food volume according to any one of above embodiments or the calculation method of food calories according to the above embodiment is achieved.

BRIEF DESCRIPTION OF THE DRAWINGS

In order to clearly illustrate the technical solution of the embodiments of the present disclosure, the drawings of the embodiments will be briefly described in the following. It is obvious that the described drawings in the following are only related to some embodiments of the present disclosure and thus are not limitative of the present disclosure.

DETAILED DESCRIPTION

Figure 1:
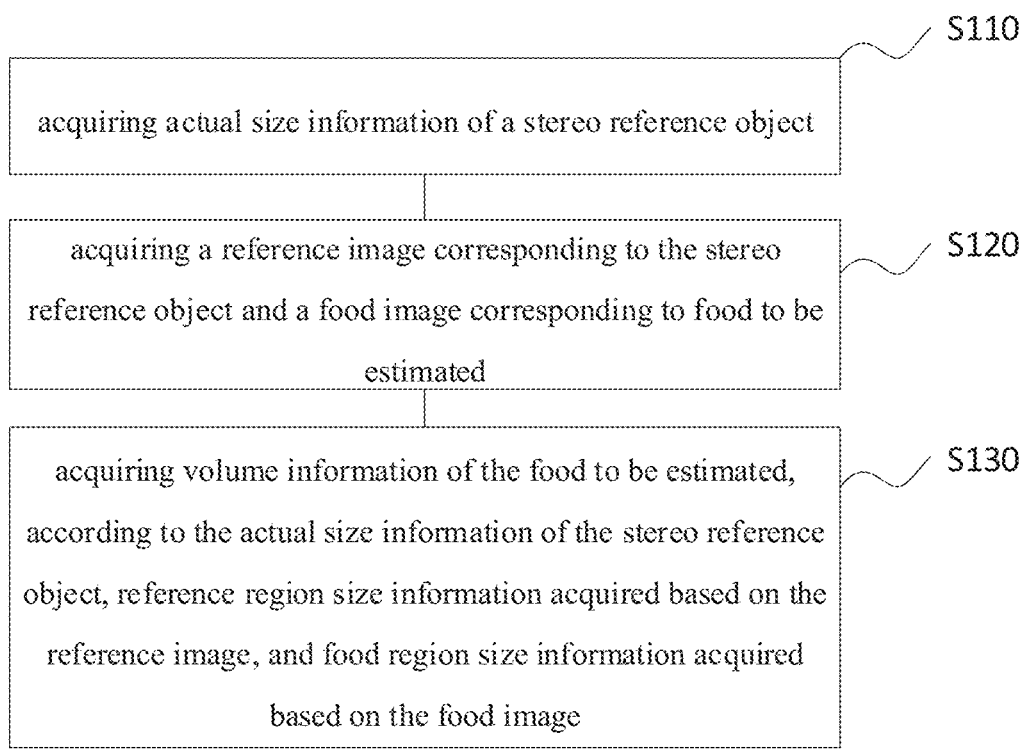
FIG. 1 is a schematic flow chart of a calculation method of food volume provided by at least one embodiment of the present disclosure.

The technical solutions in the embodiments of the present disclosure will be described clearly and completely with reference to the non-limiting exemplary embodiments shown in the drawings and detailed in the following description, and the exemplary embodiments of this disclosure and their various features and advantageous details will be more fully explained. It should be noted that the features shown in the figures are not necessarily drawn to scale. The present disclosure omits descriptions of known materials, components, and process techniques so as not to obscure example embodiments of the disclosure. The examples given are only intended to facilitate understanding of the implementation of the exemplary embodiments of the present disclosure and further enable those skilled in the art to implement the exemplary embodiments. Therefore, these examples should not be understood as limiting the scope of the embodiments of the present disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. "On," "under," "right," "left" and the like are only used to indicate relative position relationship, and when the position of the object which is described is changed, the relative position relationship may be changed accordingly.

In order to keep the following description of the embodiments of the present disclosure clear and concise, detailed descriptions of some known functions and known components are omitted in this disclosure.

Food volume can be estimated from food images and then food Calories can be obtained from the food volume. For example, food volume can be obtained according to images of a specific standard card and food in a certain angle range. This method requires a specific standard card as a reference, which limits the application scenario. In addition, the specific standard card is a flat structure, so that this method also has a requirement for image-shooting direction and needs to obtain images in a specific shooting angle range, which increases the complexity of the operation.

At least one embodiment of the present disclosure provides a calculation method of food volume. The calculation method of food volume comprises: acquiring actual size information of a stereo reference object; acquiring a reference image corresponding to the stereo reference object and a food image corresponding to food to be estimated; acquiring volume information of the food to be estimated, according to the actual size information of the stereo reference object, reference region size information acquired based on the reference image, and food region size information acquired based on the food image.

The calculation method of food volume does not limit that the reference image and the food image must be located in the same image, and does not limit the acquisition of the images in a specific image-shooting mode, which reduces the complexity of operation and enhances the flexibility of application.

The above calculation method of food volume will be explained in a non-limiting way by a plurality of embodiments and at least one example of each embodiment. As described below, different features in these specific examples or embodiments can be combined with each other without conflicting with each other, so as to obtain new examples or embodiments, which also belong to the protection scope of the present disclosure.

FIG. 1 is a schematic flow chart of a calculation method of food volume provided by at least one embodiment of the present disclosure.

For example, as shown in FIG. 1, the calculation method of food volume provided by at least one embodiment of the present disclosure includes the following steps S110 to S130.

In step S110, acquiring actual size information of a stereo reference object.

In step S120, acquiring a reference image corresponding to the stereo reference object and a food image corresponding to food to be estimated. Here, the acquired reference image allows calculating of the reference region size information of the stereo reference object, and the acquired food image allows calculating of the food region size information of the food to be estimated.

In step S130, acquiring volume information of the food to be estimated, according to the actual size information of the stereo reference object, reference region size information acquired based on the reference image, and food region size information acquired based on the food image.

For example, steps S110-S130 can be executed in sequence or in another adjusted sequences. The embodiment of the present disclosure does not limit the execution sequence of each step, and the sequence of each step can be adjusted according to an actual situation. For example, steps S110-S130 may be implemented by a server or a local terminal, which is not limited in embodiments of the present disclosure. For example, in some examples, when implementing the calculation method of food volume provided by at least one embodiment of the present disclosure, some steps in steps S110-S130 can be selectively executed, and some additional steps other than steps S110-S130 can also be executed, which is not specifically limited by the embodiments of the present disclosure.

For example, the stereo reference object may be a stereo object, volume information of which can be calculated, for example, the stereo reference object may a sphere, a cylinder, an ellipsoid, a cube, etc. For example, the stereo reference object may be selected as various items that are easy to obtain in people's life, for example, fruits such as apples or oranges, tennis balls or eggs, etc., and for example, the stereo reference object may be a hand in a fisting state that is approximately spherical. It should be noted that the shape of the stereo reference object is not limited to the standard shape, and the stereo reference object whose shape may be approximately sphere, cylindrical, or other shapes, may be used to realize the calculation method of food volume disclosed in the present disclosure, which is not limited by the present disclosure. On the other hand, in the disclosed method, the food to be estimated may be provided independently, for example, food with stable shape, such as steamed bread or bread, or food contained in a container with a certain shape, such as rice, oatmeal, meat pieces, etc., which is not limited in the disclosed embodiments.

For example, for step S110, acquiring the actual size information of the stereo reference object may be realized in various appropriate ways. For example, the size of the stereo reference object is a fixed known size stored in a database in advance, and acquiring the actual size information of the stereo reference object includes accessing to the known size stored in the database. For example, the size of a stereo reference object is a standard size, such as football, table tennis, etc., and acquiring the actual size information of the stereo reference object includes acquiring the standard size of the stereo reference object. For example, the size of the stereo reference object may be acquired by pre-calculation and stored in a database, and acquiring the actual size information of the stereo reference object includes accessing to the pre-calculated size stored in the database. For example, the size of the stereo reference object may be recalculated every time the step S110 is executed to acquire the current size information of the stereo reference object. For example, when calculating the size of the stereo reference object, one or more sizes of the stereo reference object may be obtained by way of reference objects with known sizes or directly available sizes, and then the actual size information of the stereo reference object may be calculated.

For example, in one example, acquiring a plurality of stereo reference images in which the stereo reference object is juxtaposed with a first reference object with a reference size that is acquirable, for example, the first reference object is placed beside the stereo reference object side by side, and the first reference object and the stereo reference object are kept from blocking each other during photographing process. For example, a plurality of stereo reference images are images with different shooting angles, respectively, such as a front view and a side view where the stereo reference object and the first reference object are placed side by side, and the actual size information of the stereo reference object is acquired according to the plurality of stereo reference images and the reference size of the first reference object. For example, for each of the plurality of stereo reference images, obtaining a count of first pixels corresponding to the reference size of the first reference object in the stereo reference image, obtaining a count of second pixels in at least one dimension of the stereo reference object in the stereo reference image; obtaining at least one calculated size in the at least one dimension of the stereo reference object in the stereo reference image, according to the count of the first pixels and the count of the second pixels; and acquiring the actual size information of the stereo reference object based on a plurality of calculated sizes acquired from the plurality of stereo reference images. For example, the count of the first pixels corresponding to the reference size of the first reference object in the stereo reference image may be obtained through the deep learning model. The first reference object may be, for example, any object with a known size (e.g., a certain dimension is length or width, etc.), such as a ruler (or triangle), A4 paper (or B5 paper, etc.), etc.

In another example, acquiring the actual size information of a stereo reference object, includes: acquiring a stereo reference image of the stereo reference object placed on one side of a second reference object with a reference area that is acquirable; and acquiring the actual size information of the stereo reference object, according to the stereo reference image and the reference area, for example, the stereo reference image comprises information for calculating the reference area of the second reference object. For example, if the second reference object is a planar reference object, for example, the second reference object may be any planar object with standard size, such as a piece of A4 paper (or B5 paper with a standard size), 120-type optical disc (with a diameter of 120 mm), etc., then one side of the second reference object refers to any surface of the second reference object, and the reference area refers to the reference area calculated from any surface of the second reference object. For example, if the second reference object is a three-dimensional object with a selected plane that has known sizes (such as length and width) in two dimensions, one side of the second reference object refers to the selected plane in the second reference object, and the reference area of the selected plane in the second reference object may be obtained according to the known sizes in two dimensions.

For example, for rectangular objects such as A4 paper (or B5 paper, etc.), obtaining the actual size information of the stereo reference object according to the stereo reference object image and the reference area, includes: acquiring a pixel area of the second reference object in the stereo reference image; obtaining a first mapping ratio based on the pixel area of the second reference object and the reference area; acquiring a pixel area of a region occupied by the stereo reference object in the stereo reference image; acquiring a volume of the stereo reference object according to the first mapping ratio and the pixel area of the region occupied by the stereo reference object, to obtain the actual size information of the stereo reference object. For example, in these examples, the stereo reference object may a sphere, a cylinder, an ellipsoid, a cube, etc., so according to the first mapping ratio and the pixel area of the region occupied by the stereo reference object, the actual area of the tangent plane along the central axis of the stereo reference object may be obtained, thereby the radius, major diameter, minor diameter, length and width may be obtained respectively, and the actual size of the stereo reference object may be further obtained.

For example, the second reference object is a rectangular object such as A4 paper (or B5 paper, etc.). The captured stereo reference image may have an angle error. If the pixel area of the second reference object is calculated directly by the values of pixels, the second reference object may select the range of the second reference object by using the minimum bounding rectangle, and the pixel area of the second reference object may be obtained by calculating the pixel area of the bounding rectangle, thus obtaining a more accurate area of the second reference object. For example, obtaining the pixel area of the second reference object in the stereo reference object image, includes: obtaining the minimum bounding rectangle and the pixel area of the minimum bounding rectangle, taking the pixel area of the minimum bounding rectangle as the pixel area of the second reference object. For example, pixel values of pixels corresponding to the second reference object in the stereo reference image are within a first value range, the minimum bounding rectangle of the second reference object is obtained according to the positions of pixels whose pixel values are within the first value range, and acquiring a pixel area of a region occupied by the stereo reference object in the stereo reference image, further comprises: taking pixels in the minimum bounding rectangle whose pixel values do not meet the first value range as a region occupied by the stereo reference object, to obtain the pixel area of the region occupied by the stereo reference object.

Furthermore, for example, the second reference object in the stereo reference image may be a substantially monochromatic image (e.g., monochrome (e.g., white) A4 paper, etc.), the pixel values of the pixels corresponding to the second reference object in the stereo reference image are within the first value range. Correspondingly, acquiring the pixel area of the region occupied by the stereo reference object in the stereo reference image, comprises: taking pixels in the stereo reference image whose pixel values do not meet the first value range as a region occupied by the stereo reference object, to obtain the pixel area of the region occupied by the stereo reference object; or, obtaining the pixel area of the region occupied by the stereo reference object, according to a region occupied by the stereo reference object acquired through a deep learning model. For example, target recognition is performed on the stereo reference image according to the deep learning model (such as faster-RCNN algorithm and YOLO algorithm), so as to extract the region occupied by the stereo reference object, and then obtain the pixel area of the region occupied by the stereo reference object.

For step S120, for example, one or more reference images and food images may be provided. For example, acquiring one reference image corresponding to the stereo reference object and one food image corresponding to the food to be estimated in a same image-shooting mode, for example, acquiring a plurality of reference images and a plurality of food images which are correspondingly acquired in pair according to the stereo reference object and the food to be estimated in a plurality of image-shooting modes. For example, reference images and food images may be acquired in pair in various image-shooting modes. For example, reference images and food images are shot in pair, and each pair corresponds to one image-shooting mode. Different pairs of reference image and food image may be obtained by adjusting different image-shooting modes.

For example, the reference image and the food image correspondingly acquired in pair in the same image-shooting mode are a pair of images which are corresponding to each other, that is, the reference image and the food image are independently shot in the same image-shooting mode, thereby obtaining a pair of images which are corresponding to each other. Or, the reference images and food images correspondingly acquired in pair in the same image-shooting mode belong to the same image, that is, a plurality of combination images are shot in various image-shooting modes, and each combination image includes the stereo reference object and the food to be estimated (for example, they are placed side by side in any feasible way), that is, each combination image includes the reference image and the food image, thus obtaining a pair of images corresponding to each other. In this way, the stereo reference and the food to be estimated may be placed in any feasible way as long as their images may be obtained, and in this way, the image-shooting modes of the reference image and the corresponding food image are completely the same.

The calculation method of food volume provided by at least one embodiment of the present disclosure can acquire a plurality of food images and a plurality of reference images, and the food images and the reference images are shot in the same image-shooting mode, respectively, so that it is not necessary to shoot the food to be estimated and the reference object together at the same time during image acquisition, and the food images and the reference images can be acquired separately or even in a time-sharing manner as required, so that the application scenario of the calculation method of food volume is more flexible, the operation mode is more simple and quick, and the user experience is improved.

For example, the image-shooting mode has a plurality of parameters, such as a bearing surface on which the stereo reference or the food to be estimated is placed, a shooting distance, and a shooting direction. For example, the shooting distance is the distance between the camera and the photographed object, and the shooting direction is the direction of the camera relative to the bearing surface. The shooting direction may also be understood as the angle between the connection line between the camera and the photographed object with respect to the bearing surface. For example, the shooting direction is perpendicular to or parallel to the bearing surface. For example, the image-shooting mode may also include the focal length when shooting, etc. For example, for a pair of corresponding reference image and food image that are obtained by the same shooting method, their shooting distance and shooting direction should be the same, but their bearing surfaces may be the same or different. For example, for the food images and the reference images obtained in different image-shooting modes, their shooting directions are different, and their shooting distances and bearing surfaces may be the same or different. For example, the reference image obtained for the stereo reference object in the first image-shooting mode and the food image obtained for the food to be estimated in the first image-shooting mode may be obtained separately, and the two images may not adopt the same bearing surface, but the shooting distance and shooting direction relative to the photographed object are the same in the two images, thus allowing the calculation required in the method of the embodiment of the present disclosure to be performed. Embodiments of the present disclosure are not limited to tools applicable for shooting, for example, cameras, video recorders, etc. of various specifications can be adopted.

For example, in some examples, in order to calculate the reference region size information of the stereo reference object and the food region size information of the food to be estimated, it is necessary to acquire a plurality of reference images and a plurality of food images in pair in a plurality of image-shooting modes (for example, two or more). For example, a plurality of image-shooting modes may include a first image-shooting mode and a second image-shooting mode, the shooting directions of these two image-shooting modes are different, and the shooting direction of the first image-shooting mode and the shooting direction of the second image-shooting mode cross each other, that is, the shooting direction of the first image-shooting mode and the shooting direction of the second image-shooting mode have a certain included angle, for example, the included angle may be any angle between 0 and 90 degrees. Therefore, the size information of the photographed object in at least two dimensions may be obtained by analyzing the photographed image, for example, the length information, the width information and the height information of the photographed object may be obtained by an image detection and recognition method. Correspondingly, a plurality of reference images include a first reference image obtained in the first image-shooting mode and a second reference image obtained in the second image-shooting mode, and the first reference image and the second reference image enables the calculation of the reference region size information of the stereo reference object. The plurality of food images comprise a first food image obtained in the first image-shooting mode and a second food image obtained in the second image-shooting mode, and the first food image and the second food image enable the calculation of the food region size information of the food to be estimated. The shooting direction is not limited to meet specific requirements, so that the operation difficulty of users is reduced and the application flexibility is enhanced.

For example, the shooting direction of the first image-shooting mode and the shooting direction of the second image-shooting mode are perpendicular to each other, and the shooting direction of the first image-shooting mode is perpendicular to the bearing surface of the first image-shooting mode, and the shooting direction of the second image-shooting mode is parallel to the bearing surface of the second image-shooting mode. In these two ways, the bearing surfaces may be the same bearing surface or parallel to each other, so that the front view of the object (i.e., stereo reference object and food to be estimated) can be obtained in the first shooting way, while the side view of the object can be obtained in the second shooting way, and the volume of the food to be estimated can be calculated according to the size (e.g., bottom area) obtained in the front view and the size (e.g. height or thickness) obtained in the side view.

For example, in at least one example, acquiring a plurality of reference images and a plurality of food images which are correspondingly in pair according to the stereo reference object and the food to be estimated in a plurality of image-shooting modes, includes: continuously shooting a plurality of images where the food to be estimated and the stereo reference object are simultaneously located on the same bearing surface, and extracting a plurality of key images from the plurality of images to obtain the plurality of reference images and the plurality of food images, for example, each of the plurality of key images comprises a reference image and a food image that are corresponding to each other. More comprehensive information of food to be estimated can be obtained by continuously shooting the plurality of images, and thus more accurate calculation results of volume of food to be estimated can be obtained.

For example, continuously shooting a plurality of images where the food to be estimated and the stereo reference object are simultaneously located on a same bearing surface, extracting a plurality of key images from the plurality of images, comprises: for each image of the plurality of images, extracting a to-be-estimated food region occupied by the food to be estimated, and obtaining a pixel area of the to-be-estimated food region corresponding to each image; according to the pixel area of the to-be-estimated food region corresponding to each image, extracting an image whose pixel area of the to-be-estimated food region is larger than a preset threshold as one of the plurality of key images from the plurality of the images, for example, the plurality of key images at least comprises a first key image and a second key image, the first key image comprises the first food image and the first reference image, and the second key image comprises the second food image and the second reference image. For example, by shooting video, a plurality of images of food to be estimated and stereo reference object located on the same bearing surface can be continuously shot. The relative change here refers to the difference of pixel areas of to-be-estimated food regions among the plurality of images. For example, after obtaining the pixel areas of to-be-estimated food regions in the plurality of images, these images are sorted according to the size of the pixel areas of to-be-estimated food regions (e.g. ascending or descending order), and then a reference image is selected, and in this sequence, an image whose pixel area change relative to the to-be-estimated food region in the reference image larger than a preset threshold is selected as the first key image, and several key images are obtained by analogy. The image with a large pixel area difference in the pixel area of the to-be-estimated food region is selected as the key image from the plurality of images, which can obtain better food volume estimation results on the premise of reducing the number of image analysis.

For step S130, the reference region size information of the stereo reference object can be calculated according to the reference image, and the food region size information of the food to be estimated can be calculated according to the food image, so that the volume information of the food to be estimated can be obtained according to the actual size information of the stereo reference object, the reference region size information and the food region size information.

For example, in at least one of the above examples, the volume information of the food to be estimated can be obtained according to the actual size information of the stereo reference object, the first reference image, the second reference image, the first food image and the second food image.

For example, the food to be estimated is contained in a container with a certain shape. Acquiring the volume information of the food to be estimated, according to the actual size information of the stereo reference object, the reference region size information, and the food region size information, comprises: for each of the plurality of reference images, acquiring a pixel area of a region occupied by the stereo reference object in the reference image, to obtain the reference region size information of the stereo reference object; acquiring a second mapping ratio, according to the reference region size information of the stereo reference object and the actual size information of the stereo reference object; extracting the to-be-estimated food region occupied by the food to be estimated in the first food image, to obtain the food region size information; acquiring food size information according to the food region size information and the second mapping ratio; for the plurality of food images, extracting to-be-estimated food regions occupied by the food to be estimated in the plurality of food images, and determining a container shape of the food to be estimated according to the to-be-estimated food regions; acquiring the volume information of the food to be estimated according to the container shape of the food to be estimated and the food size information. For example, for the second food image, extracting the to-be-estimated food region occupied by the food to be estimated, and determining the height value of the food to be estimated according to the to-be-estimated food region in the second food image and the second mapping ratio; and acquiring the volume information of the food to be estimated according to the container shape of the food to be estimated, the height value of the food to be estimated and the food size information.

For example, in the above examples, obtaining the pixel area of the region occupied by the stereo reference object in each of the plurality of reference images to obtain the reference region size information of the stereo reference object, includes: for each reference image, extracting the region occupied by the stereo reference object (for example, according to a deep learning model), and obtaining the pixel area of the region occupied by the stereo reference object corresponding to each reference image; calculating an average value of all acquired pixel areas of the regions occupied by the stereo reference object in the plurality of reference images, to obtain the reference region size information of the stereo reference object. The deep learning model applied here, for example, is trained by using training data in advance, and can divide the image into regions.

For example, in the above examples, determining a height value of the food to be estimated according to the to-be-estimated food region in the second food image and the second mapping ratio, comprises: acquiring a count of pixels corresponding to each column of pixels in the to-be-estimated food region; determining a height component of the food to be estimated according to the count of pixels corresponding to each column of pixels; and determining the height value of the food to be estimated according to the height component and the second mapping ratio.

For example, for the plurality of food images, determining the container shape of the food to be estimated according to the to-be-estimated food region corresponding to each of the plurality of food images, includes: obtaining a standard container recognition model (for example, a deep learning model), and determining the container shape of the food to be estimated according to the plurality of food images and the standard container recognition model. For example, the deep learning model may be trained by using training data including various container shapes in advance, thereby detecting the container shape of the input image, such as dish-shaped, hemispherical, truncated cone, etc. After obtaining the container shape, the volume can be calculated according to the shape.

For example, in the above embodiments, for an image to be processed including the food to be estimated, extracting a to-be-estimated food region occupied by the food to be estimated, comprises: dividing the image to be processed into a plurality of region sets, and performing similarity calculation on each region set of the plurality of region sets, to obtain a similarity value of each region set; merging region sets with similarity values meeting a preset threshold to obtain a plurality of merged regions; taking a closed region out of the plurality of merged regions with the largest pixel area as the to-be-estimated food region of the image to be processed. Here, the similarity calculation comprises one or more combinations of color similarity calculation, texture similarity calculation, size similarity calculation and overlap similarity calculation.

For example, for an image to be processed including the food to be estimated, extracting a to-be-estimated food region occupied by the food to be estimated, comprises: performing edge recognition on the image to be processed based on a depth convolution network model, to obtain the to-be-estimated food region of the food to be estimated in the image to be processed.

For example, in at least one example, performing edge detection on the first reference image and the second reference image through a deep learning model, and obtaining the pixel area of the region occupied by the stereo reference object in each reference image, to obtain the reference region size information of the stereo reference object, for example, calculating an average value of the pixel areas occupied by the stereo reference object in the two reference images, to obtain the reference region size information of the stereo reference object; obtaining a second mapping ratio, according to the reference region size information of the stereo reference object and the actual size information of the stereo reference object; then, for the first food image, performing edge detection through the deep learning model to extract the to-be-estimated food region occupied by the food to be estimated, and acquiring the shape and size of the to-be-estimated food region. For example, if the to-be-estimated food region is circular, the maximum width of the to-be-estimated food region is detected as the diameter of the to-be-estimated food region, and then obtaining the true diameter of the food to be estimated based on the second mapping ratio as the food size information. Target recognition is carried out on the plurality of food images through a pre-trained deep learning model (such as faster-RCNN algorithm or YOLO algorithm), so as to obtain the container shape of the food to be estimated, for example, the container of food to be estimated is a pot, bowl, etc., whose shape can be approximately hemispherical; and acquiring the volume information of the food to be estimated, according to the food size information and the container shape of the food to be estimated, for example, according to the hemispherical volume calculation formula and the true diameter of the food to be estimated, the volume information of the food to be estimated can be obtained.

For example, in other examples, step S130 may further include obtaining a second mapping ratio, according to the reference region size information of the stereo reference object and the actual size information of the stereo reference object; identifying the food to be estimated in the plurality of food images by means of a deep learning model (such as Faster R-CNN model), so as to acquire the edge recognition result and the type of the food to be estimated. For example, the food region size information of the food to be estimated may be obtained according to the edge recognition result, and the food size information may be obtained according to the food region size information and the second mapping ratio. According to the type of the food to be estimated, the shape of the food to be estimated may be obtained, and the volume information of the food to be estimated may be obtained according to the food size information and the shape of the food to be estimated. For example, the food size information includes the area of the food to be estimated, for example, it is found that the food to be estimated is detected as an apple through a deep learning model, since the apple can be approximately seen as spherical, the volume information of the food to be estimated can be obtained.

In addition, it should be noted that, for step S130, the acquired reference images are applicable to calculate the reference region size information of the stereo reference object, and the acquired food images are applicable to calculate the food region size information of the food to be estimated. The present disclosure does not limit the executors of obtaining the reference region size information based on reference images and obtaining the food region size information based on food images. For example, steps S110-S130 are performed by the mobile terminal, and in this case, the reference region size information of the stereo reference object and/or the food region size information of the food to be estimated can be calculated by the mobile terminal, or calculated by the server and then sent to the mobile terminal.

For example, in other examples, the acquired food image and reference image are images taken directly above the stereo reference object and the food to be estimated, that is, the shooting directions of these images are perpendicular to the bearing surface of the food to be estimated. The food to be estimated is placed in a container, and the container shape of the food to be estimated is known or can be determined according to one food image. In this case, only one food image and one reference image are needed to complete the calculation of the volume information of the food to be estimated. Acquiring volume information of food to be estimated according to actual size information of the stereo reference object, reference region size information and food region size information, includes: acquiring a pixel area of a region occupied by the stereo reference object in the one reference image, to obtain reference region size information of the stereo reference object; obtaining a second mapping ratio, according to the reference region size information of the stereo reference object and the actual size information of the stereo reference object; for the one food image, extracting the to-be-estimated food region occupied by the food to be estimated, to obtain the food region size information; obtaining food size information according to the food region size information and the second mapping ratio; obtaining the volume information of the food to be estimated, according to the container shape of the food to be estimated and food size information of the food to be estimated.

Hereinafter, the calculation method of food volume provided by the present disclosure will be explained in detail by taking the hand in a fisting state which can be approximately seen as a sphere and the second reference object which is a piece of paper with a standard size as an example. For example, the hand in the fisting state is processed as a standard sphere, but the embodiment of the present disclosure is not limited to this. For example, a hand in the fisting state can also be processed as an ellipsoid or a triangular prism, thereby obtaining the required size information and approximate volume, and the volume may be used to estimate food volume.

It should be noted that the present disclosure does not limit the types of processed image. In some embodiments, the processed image may be a color image or a black-and-white grayscale image, or even a binary image in some examples. For a color image, the pixel values of pixels mentioned in the present disclosure include a set of RGB pixel values, while for black-and-white grayscale images, the pixel values of pixels are expressed as grayscale values.

In Step S110, acquiring actual size information of a stereo reference object.

For example, in some examples, first, the hand in the fisting state is placed on a side of the second reference object where the reference area can be calculated, for example, shooting the stereo reference image in which the stereo reference object is located on the front side of the second reference object, and the stereo reference image includes information used for calculating the reference area in the second reference object. For example, the second reference object is a piece of monochrome (e.g., white) paper with a standard size, such as A4 paper or B5 paper, etc. For example, patterns or other color patterns may present on the second reference object, but the area of patterns or other color patterns should not exceed 5% of the total area of the second reference object, so as to avoid a large detection error when detecting the stereo reference object. For example, shooting the stereo reference image in which a hand in a fisting state is placed in front of a piece of monochrome paper with a standard size, and the stereo reference image includes all information of A4 paper, that is, all length and all width information of A4 paper (the A4 paper may also be partially blocked).

Figure 2:
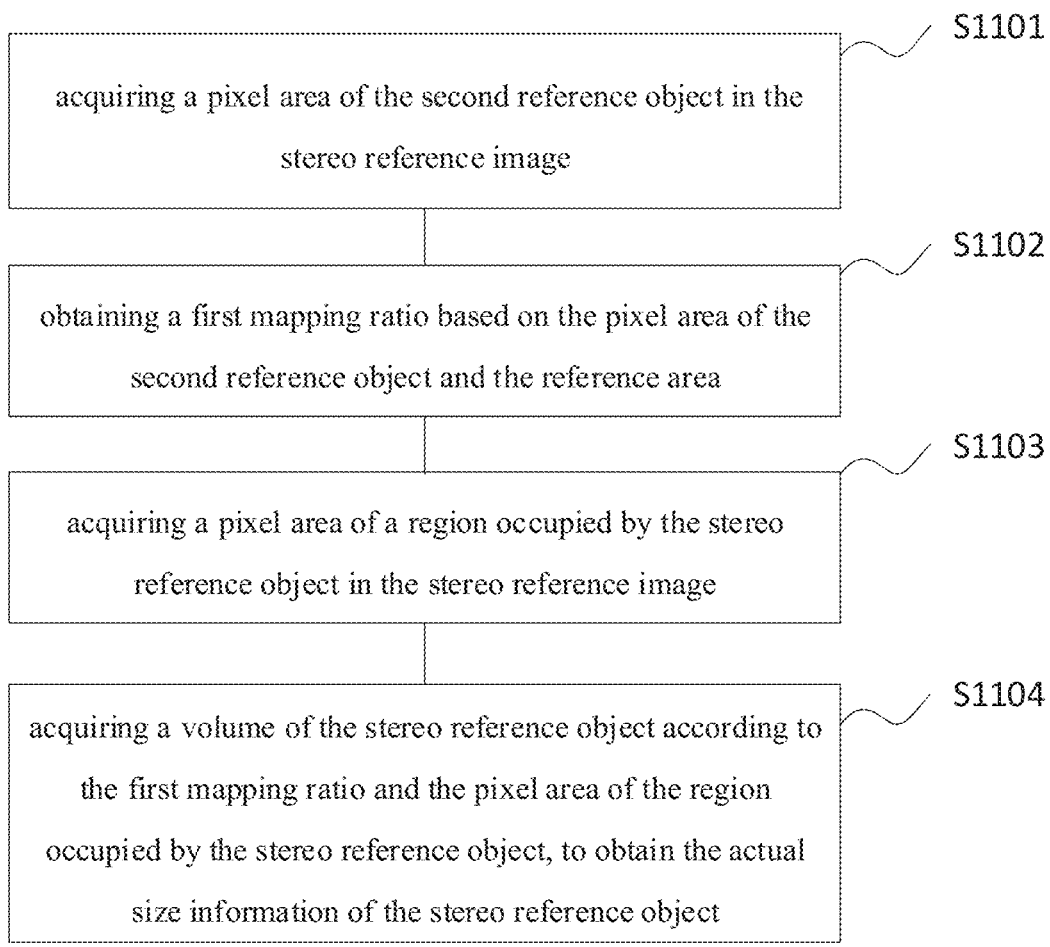
FIG. 2 is an example flow chart of step S110 in the calculation method of food volume shown in FIG. 1.

The actual size information of the stereo reference object is obtained according to the stereo reference image and the reference area of the second reference object. For example, in at least one embodiment of the present disclosure, as shown in FIG. 2, the step S110 may specifically include steps S1101-S1104.

In step S1101, acquiring a pixel area of the second reference object in the stereo reference image.

For example, the second reference is a piece of monochrome paper (e.g., white, green, yellow, etc.) with a standard size. For example, the second reference object is a piece of white A4 paper with a size of 210 mm×297 mm, so the reference area SA4 of the second reference object is 623.7 cm². In order to better use the A4 paper as a reference object, the area of the A4 paper is used instead of the length and width of the A4 paper for calculation, thus avoiding the adverse effects of distortion caused by shooting angle when shooting images. In the stereo reference image, the pixel values of the pixels corresponding to the second reference object are within the first value range (here, the first value range is the range corresponding to white, for example, R pixel value range is 250-255, G pixel value range is 250-255, B pixel value range is 250-255), and the positions of the pixels in the stereo reference image whose pixel values meet the first value range are obtained. According to the positions of these pixels, the pixel area $S_{rectangel}$ of the second reference object may be acquired.

In step S1102, obtaining a first mapping ratio based on the pixel area of the second reference object and the reference area.

For example, the first mapping ratio may be calculated according to formula (1):

$$scale_1 = \frac{SA4}{S_{rectangel}} \qquad \text{formula (1)}$$

In step S1103, acquiring a pixel area of a region occupied by the stereo reference object in the stereo reference image.

For example, in some examples, the wrist part of the hand in the fisting state in the stereo reference image is at the edge of the second reference object, the area occupied by the stereo reference object may be obtained according to the color difference between the hand in the fisting state and the second reference object, that is, in the stereo reference image, the pixel value range of the pixels corresponding to the hand in the fisting state is different from that of the pixels corresponding to the second reference object, a fist region occupied by the hand in the fisting state may be obtained by detecting the pixel values of pixels in the stereo reference image.

For example, the second reference object is a piece of monochrome (e.g., white) paper with a standard size, taking pixels in the stereo reference image whose pixel values do not meet the first value range as a fist region, and obtaining the pixel area of the fist region as the pixel area $S_{ref}$ of the region occupied by the stereo reference object (i.e., the hand in the fisting state).

In step S1104, acquiring a volume of the stereo reference object according to the first mapping ratio and the pixel area of the region occupied by the stereo reference object, to obtain the actual size information of the stereo reference object.

Since the hand in the fisting state can be approximately seen as a sphere, the orthographic projection of the hand in the stereo reference image can be approximately circular, through the circular area calculation formula, according to the first mapping ratio $scale_1$ and the pixel area $S_{ref}$ of the region occupied by the stereo reference object, the radius r of the stereo reference object may be calculated according to formula (2):

$$r = \sqrt{\frac{S_{ref} * scale_1}{\pi}} \qquad \text{formula (2)}$$

After obtaining the radius r of the stereo reference object, according to the formula (3) for calculating the volume of the sphere, the actual size information of the hand in the fisting state, that is, the actual size information of the stereo reference object, is calculated.

$$V = \tfrac{4}{3}\pi r^3 \qquad (3)$$

For example, in other examples, a colored stereo reference image such as a hand in a fisting state can be grayed out first to obtain a black-and-white grayscale image; then binarizing the grayscale image to obtain an intermediate binary image; finally, performing image erosion and image expansion process on the intermediate binary image, and filling the small holes in the intermediate binary image to obtain the binary image of the stereo reference object. For example, when step S110 is executed, in step S1101, the positions of pixels whose grayscale values of pixels in the binary image of the stereo reference object satisfy the first value range (for example, the second reference object is white A4 paper, and the first value range is 250-255) are obtained, and the pixel area $S_{rectangle}$ of the second reference object is obtained according to the positions of these pixels. Then, steps S1102-S1104 are executed to obtain the actual size information of the stereo reference object.

For example, in other examples, the wrist part of the hand in the fisting state in the stereo reference image is not at the edge of the second reference object, and the stereo reference image includes the hand in the fisting state and the arm part. Since the region occupied by the hand in the fisting state in the stereo reference image includes not only the hand in fisting state which can be approximately seen as a sphere, but also the long arm part, it is necessary to acquire the fist image through a hand detection model, extract the fist region in the fist image, and try to remove the arm part to reduce the calculation error. For example, when step S110 is executed, step S1101 is first executed to obtain the pixel area of the second reference object in the stereo reference image. Then, step S1102 is executed to calculate the first mapping ratio. Then, in step S1103, a fist image is acquired through the hand detection model, a fist region in the fist image is extracted, and the pixel area of the fist region is obtained as the pixel area $S_{ref}$ of the region occupied by the stereo reference object (that is, the hand in the fisting state). Finally, step S1104 is executed to obtain the actual size information of the stereo reference object.

For comparison, for example, in other examples, the second reference object is a monochromatic background plate (e.g., a 120-type optical disc printed in black), and the shape of the second reference object may not be rectangular. For example, when step S110 is executed, the shape (e.g., circle) of the second reference object may be identified through the deep learning model, and the second reference region may be extracted and the pixel area of the second reference region may be obtained, so that the first mapping ratio may be obtained based on the pixel area of the second reference region and the reference area of the second reference object. Then, detecting the positions of pixels with different pixel values from the second reference object in the second reference region (for example, pixels with R pixel value not 0, G pixel value not 0, and B pixel value not 0), and obtaining the pixel area $S_{ref}$ of the region occupied by the stereo reference object (for example, the hand in the fisting state) according to these positions. Finally, step S1104 is executed to obtain the actual size information of the stereo reference object.

Next, in step S120, acquiring a reference image corresponding to the stereo reference object and a food image corresponding to food to be estimated.

For example, the food to be estimated and the hand in the fisting state are placed on the same bearing surface at the same time, for example, the hand in the fisting state is placed beside the food to be estimated side by side, and the food to be estimated and the hand in the fisting state are kept from blocking each other in the shooting process. A plurality of images in which the food to be estimated and the hand in the fisting state are placed on the same bearing surface at the same time are continuously shot, and during the shooting process, the food to be estimated and the hand in the fisting state should be kept at the same horizontal plane and do not block each other. For example, a plurality of images of food to be estimated and hands in the fisting state are continuously shot on the same bearing surface by shooting a video. For example, by means of video shooting or other continuous shooting, a video may be taken from the direction perpendicular to the bearing surface where the food to be estimated and the hand in the fisting state are located, until the direction parallel to the bearing surface where the food to be estimated and the hand in the fisting state are located, thus obtaining a plurality of images, each of the plurality of images includes a corresponding pair of reference image and food image. Because the hand in the fisting state can be approximately seen as a sphere, the detection effect will not be affected due to different shooting angles of the camera when collecting video.

Then, extracting a plurality of key images from the plurality of images to obtain the plurality of reference images and the plurality of food images. For example, for each image of the plurality of images, extracting a to-be-estimated food region occupied by the food to be estimated, and obtaining a pixel area of the to-be-estimated food region corresponding to each image; according to the pixel area of the to-be-estimated food region corresponding to each image, extracting an image in which a relative change of the pixel area of the to-be-estimated food region is larger than a preset threshold as one of the plurality of key images from the plurality of the images. The preset threshold may be selected in advance according to experience, for example, 10%~50%, and the number of key images is greater than or equal to 3. After obtaining the pixel areas of the to-be-estimated food regions in a plurality of images, these images are sorted according to the size of the pixel areas of the to-be-estimated food regions (for example, ascending or descending order). Then selecting a reference image, and in this sequence, selecting an image whose relative change in the pixel area with respect to the reference image is greater than a preset threshold as the first subsequent image, and selecting an image whose relative change in the pixel area with respect to the first subsequent image is greater than a preset threshold as the second subsequent image, so that a plurality of key images are obtained by analogy.

For example, in one embodiment, firstly, an image whose shooting direction is perpendicular to the bearing surface where the to-be-estimated food and the hand in the fisting state is extracted as the first key image; then, an image whose shooting direction is parallel to the bearing surface where the to-be-estimated food and the hand in the fisting state is extracted as the second key image; then, an image whose relative change in the pixel area with respect to the first key image is greater than 20% as the third key image; then, an image whose relative change in the pixel area with respect to the third key image is greater than 20% as the fourth key image, so that a plurality of key images are obtained by analogy.

For example, each of the plurality of key images includes the information of the food to be estimated and the information of the hand in the fisting state, so that each key image includes a corresponding pair of reference image and food image. A food image is obtained by removing the hand part in the key image, so as to obtain a plurality of corresponding reference images and food images according to a plurality of key images.

Finally, in step S130, acquiring volume information of the food to be estimated, according to the actual size information of the stereo reference object, reference region size information acquired based on the reference image, and food region size information acquired based on the food image.

Figure 3A:
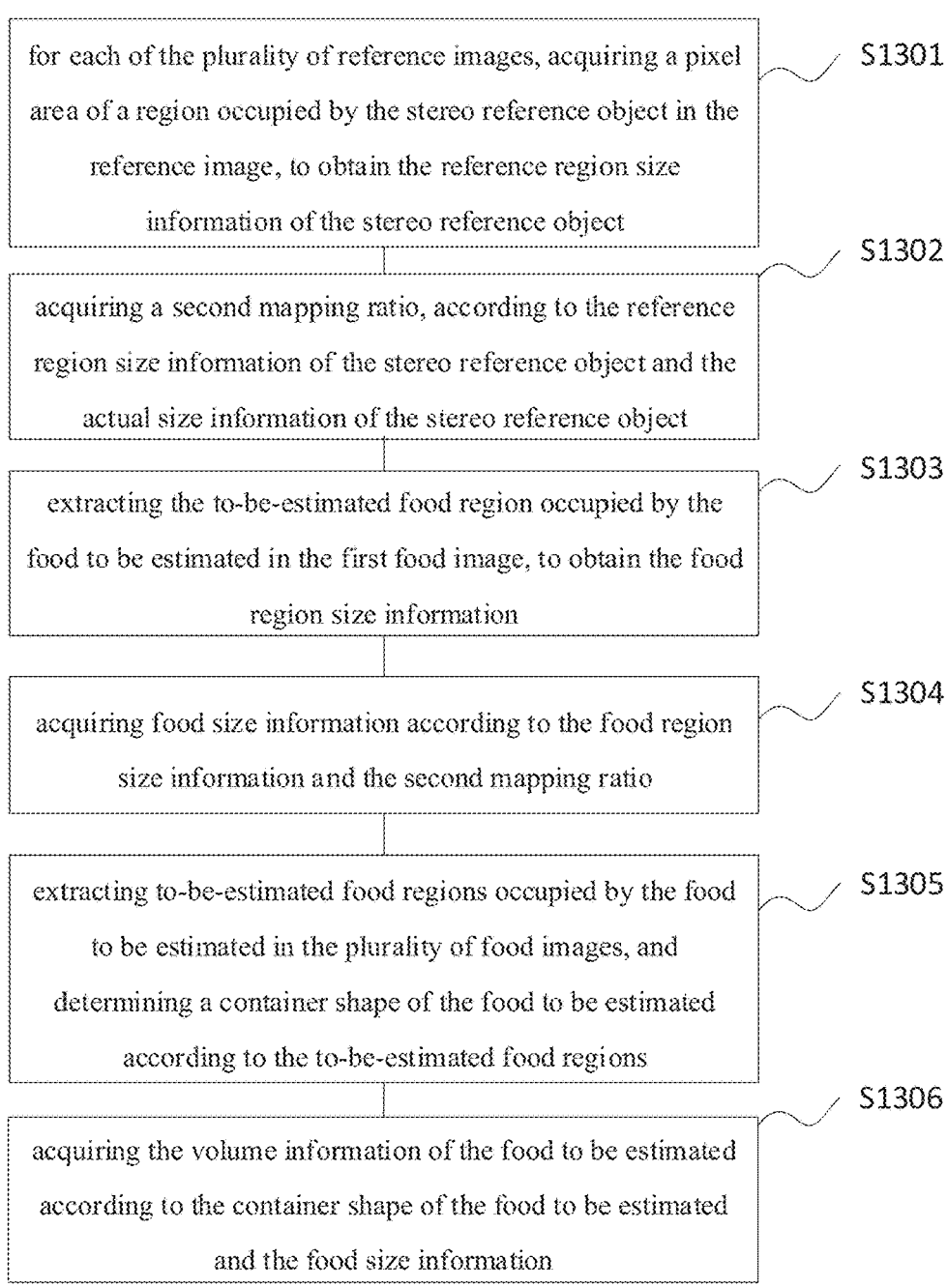
FIG. 3A is an example flow chart of step S130 in the calculation method of food volume shown in FIG. 1.

FIG. 3A is an example flow chart of step S130 in the calculation method of food volume shown in FIG. 1. As shown in FIG. 3A, an example of step S130 in the calculation method of food volume may specifically include step S1301 to step S1306.

First, in step S1301, for each of the plurality of reference images, acquiring a pixel area of a region occupied by the stereo reference object in the reference image, to obtain the reference region size information of the stereo reference object.

For example, in some examples, the region of the stereo reference object (such as the hand in the fisting state) may be extracted from each reference image through a deep learning model (such as faster-RCNN algorithm, YOLO algorithm, etc.), and the pixel area of the region occupied by the stereo reference object corresponding to each reference image may be obtained. Then, calculating the average value of all acquired pixel areas of the regions occupied by the stereo reference object to obtain the reference region size information of the stereo reference object.

For example, in other embodiments, for each of the plurality of reference images, acquiring a fist image according to a hand detection model from the reference image, extracting a fist region of the fist image, and acquiring a pixel area of the fist region; then calculating an average value of all acquired pixel areas of the fist regions in the plurality of reference images, to obtain the reference region size information of the stereo reference object. Then, in step S1302, acquiring a second mapping ratio, according to the reference region size information of the stereo reference object and the actual size information of the stereo reference object.

In the above example, the stereo reference object is a hand in a fisting state that may be approximately seen as a sphere, so the real area $S_{hand}$ of the hand in the fisting state may be calculated according to the actual size information of the stereo reference object, and the reference region size information of the stereo reference object is the pixel area $S_{pix}$ of the region occupied by the hand in the fisting state. The second mapping ratio may be calculated according to formula (4):

$$scale_2 = \frac{S_{hand}}{S_{pix}} \quad \text{formula (4)}$$

Next, in step S1303, extracting the to-be-estimated food region occupied by the food to be estimated in the first food image, to obtain the food region size information.

For example, the first food image is an image whose shooting direction is perpendicular to the bearing surface where the food to be estimated is located, that is, a top view of the food to be estimated.

For example, in some examples, when extracting the to-be-estimated food region occupied by the food to be estimated in the first food image, regions with similar characteristics such as color and texture may be obtained by means of the similarity calculation method, and the closed region with the largest area is selected as the to-be-estimated food region. For example, first, dividing the first food image into a plurality of region sets, and calculating the similarity of each region set to obtain the similarity value of each region set; then, merging the region sets whose similarity values meet the preset similarity threshold, to obtain a plurality of merged regions; finally, the closed region with the largest pixel area among the merged regions is selected as the to-be-estimated food region in the first food image.

After obtaining the to-be-estimated food region in the first food image, extracting the pixel area of the to-be-estimated food region as the food region size information. For example, if the food images are taken by placing the food to be estimated in a hemispherical bowl, the top view information of the food to be estimated obtained from the first food image is a circular to-be-estimated food region, and the pixel area of the to-be-estimated food region is extracted as the food region size information.

For example, the similarity calculation method may use selective search algorithm to segment the to-be-estimated food image, so as to obtain the to-be-estimated food image. The selective search algorithm may include the following operations:

Firstly, calculating the dissimilarity between each pixel and the pixel satisfying the connected region relationship.

For example, if the connected region relationship is four-connected region, calculating the dissimilarity between each pixel and its upper, lower, left and right pixels. For example, if the connected region relationship is eight-connected region, calculating the dissimilarity between each pixel and its upper, lower, left, right, upper left, lower left, upper right and lower right pixels.

For example, the dissimilarity calculation may include one or more combinations of color similarity calculation, texture similarity calculation, size similarity calculation, and overlap similarity calculation. For example, the dissimilarity is the sum of the color dissimilarity, texture dissimilarity, size dissimilarity, and overlap dissimilarity overlaying a corresponding weight values.

It should be noted that the connecting line between two pixels is called an edge, each edge corresponds to pixels $v_i$ and $v_j$, and each edge corresponds to a dissimilarity value which represents the dissimilarity between the pixels corresponding to the edge.

Then, the edges are arranged in ascending order according to the size of the dissimilarity value to obtain the edge set.

Then, traversing the edge set to implement merge judge of each edge element.

For example, if the pixel $v_i$ and the pixel $v_j$ corresponding to the edge element do not belong to the same region, and the dissimilarity value corresponding to the edge element is not greater than the dissimilarity within the pixel $v_i$ and the pixel $v_j$, merging the pixel $v_i$ and the pixel $v_j$ into the same region, otherwise, traversing the next edge element and implementing the merge judge on the next edge element until traversing to the last edge element.

It should be noted that more information about the selective search algorithm can refer to the conventional design, and the above description of the present disclosure is only a schematic introduction.

For example, in other examples, when extracting the to-be-estimated food region occupied by the food to be estimated, firstly, extracting a rough range of the to-be-estimated food region according to the deep learning model, and then obtaining the to-be-estimated food region by similarity calculation method. In this way, the to-be-estimated food region is extracted by combining deep learning with similarity calculation, which can delete the irrelevant background except the to-be-estimated food region and reduce the calculation error. In addition, when the to-be-estimated food region is contained in the container, the method can also reduce the calculation error when the food to be estimated in the container is not full.

Then, in step S1304, acquiring food size information according to the food region size information and the second mapping ratio.

For example, a plurality of food images are taken by placing the food to be estimated in a hemispherical bowl, the food region size information of the first food image is the pixel area $S_f$ of the to-be-estimated food region; according to the second mapping ratio, the real area of the to-be-estimated food region may be obtained by formula $S_f*scale_2$, and the real radius r of the to-be-estimated food region, that is, the food size information, may be obtained through the circular area calculation formula.

Then, in step S1305, extracting to-be-estimated food regions occupied by the food to be estimated in the plurality of food images, and determining a container shape of the food to be estimated according to the to-be-estimated food regions.

For example, in some examples, a standard container recognition model is obtained based on a deep learning model, and the container shape of the food to be estimated is determined according to the plurality of food images and the standard container recognition model. For example, based on the target recognition algorithm (such as faster-RCNN algorithm or YOLO algorithm) in the deep learning model, the model for recognizing common container data sets such as pot, bowl, plate and basin may be trained to acquire a standard container recognition model. A plurality of food images are input into the standard container recognition model for container type recognition to obtain the container shape of the food to be estimated.

Figure 3B:
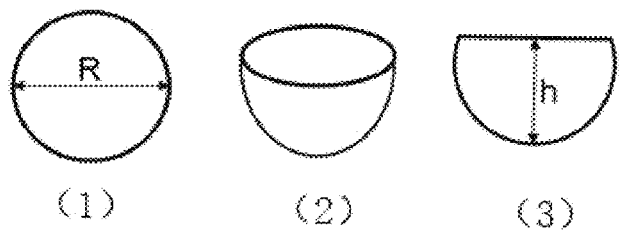
FIG. 3B is a standard container image of a hemispherical bowl provided by at least one embodiment of the present disclosure.

For example, in other examples, calculating the Euclidean distance between the food image and the edge of the standard container image of the standard container that is stored in the database in advance, and determining the container shape of the food to be estimated according to the Euclidean distance corresponding to different standard containers. For example, the standard container set in the database stores a plurality of standard container images, and each standard container image may include images of different angles. For example, as shown in FIG. 3B, the standard container image of a hemispherical bowl as an example of a standard container includes: (1) an image (front view) perpendicular to the viewing angle of the bearing surface where the bowl is located; (2) an image (perspective view) with an included angle of 45 degrees from the bearing surface where the bowl is located; (3) an image (side view) parallel to the viewing angle of the bearing surface where the bowl is located.

Firstly, extracting a food image, which is in a same corresponding direction as a q-th standard container in a standard container set, from the plurality of food images, to obtain at least one to-be-estimated container image corresponding to the q-th standard container. For example, extracting a first food image and a second food image from a plurality of food images as to-be-estimated container image corresponding to a hemispherical bowl.

Then, for each of the at least one to-be-estimated container image, extracting a to-be-estimated food region occupied by the food to be estimated, respectively. For example, for the first food image and the second food image, the method for extracting the to-be-estimated food region as described in step S1303 is used to extract the to-be-estimated food region occupied by the food to be estimated. For example, a deep learning model algorithm, a similarity calculation method or an algorithm combining deep learning model and similarity calculation can be adopted, which will not be described in detail here.

Then, calculating a Euclidean distance between the to-be-estimated food region of the to-be-estimated container image and a shape edge of the q-th standard container in a corresponding direction, to obtain at least one Euclidean distance value. For example, calculating the first Euclidean distance between the first food image and the shape edge of the hemispherical bowl numbered (1) in the standard container image shown in FIG. 3B, and calculating the second Euclidean distance between the second food image and the shape edge of the hemispherical bowl numbered (3) in the standard container image shown in FIG. 3B.

Then, overlaying Euclidean distance values corresponding to all directions of the q-th standard container with preset weight values corresponding to all directions to obtain a plurality of superposition results, and summing the plurality of superposition results to obtain the Euclidean distance sum value corresponding to the q-th standard container. For example, summing the product of the first Euclidean distance and the first weight value, and the product of the second Euclidean distance and the second weight value, to obtain the Euclidean distance sum value corresponding to the q-th hemispherical bowl.

Finally, detecting a minimum Euclidean distance sum value in a Euclidean distance sum value set corresponding to the standard container set, and taking a standard container corresponding to the minimum Euclidean distance sum value as the container shape of the food to be estimated. For example, Euclidean distance sum value sets corresponding to all the standard containers in the standard container set are calculated according to the above steps, and the Euclidean distance sum value corresponding to the hemispherical bowl is the smallest, so that the container shape of the food to be estimated is a bowl.

In step S1306, acquiring the volume information of the food to be estimated according to the container shape of the food to be estimated and the food size information.

For example, if the container shape of the food to be estimated is a bowl or pot that is approximately hemispherical, the volume information of the food to be estimated can be obtained according to the true radius r of the to-be-estimated food region and the calculation formula of the hemisphere.

For example, in some examples, the container shape of the food to be estimated is a pot that can be approximately seen as a cylinder. Since the volume calculation of the cylinder requires a height value, step S130 may further include: extracting the to-be-estimated food region occupied by the food to be estimated in the second food image, and determining a height value of the food to be estimated according to the to-be-estimated food region in the second food image and the second mapping ratio. In this case, in step S1306, the volume information of the food to be estimated is obtained according to the container shape of the food to be estimated, the height value and the food size information. For example, the food size information includes the true radius r of the food to be estimated, and the volume of the food to be estimated may be obtained according to the volume calculation formula of cylinder, the true radius r of the food to be estimated and the height value of the food to be estimated.

For example, in some examples, determining a height value of the food to be estimated may be implemented by acquiring a count of pixels corresponding to each column of pixels in the to-be-estimated food region. For example, selecting the maximum value among the counts of pixels corresponding to all columns of pixels in the to-be-estimated food region as the height component of the food to be estimated, and the product of the height component and the second mapping ratio is taken as the height value of the food to be estimated.

For example, in some examples, since the shooting direction of the second food image is not necessarily completely parallel to the bearing surface of the food to be estimated, there may be a big error between the height component obtained by the maximum value in the number of pixels and the actual height, so the height value of the food to be estimated may be obtained from the height components of the two edges of the to-be-estimated food region. Because the change of angle has little influence on the length of the two edges of the cylinder during shooting, the obtained height value is more accurate. For example, the number of pixels corresponding to each column of pixels is arranged according to the acquisition order to obtain a sequence of column pixel numbers; extracting the first p elements and the last m elements in the sequence, and calculating the average value of the p elements and the m elements as the height component of the food to be estimated; and taking the product of the height component and the second mapping ratio as the height value of the food to be estimated.

For example, in other embodiments, shooting a top image whose shooting direction is perpendicular to the bearing surface where the hand in the fisting state and the food to be estimated are placed side by side, and the top image includes a reference image and a food image. The step S130 in the calculation method of food volume may include: for the reference image in the top image, acquiring the minimum bounding rectangle of the hand in the fisting state in the reference image, detecting the length and width of the minimum bounding rectangle through a deep learning model, and then calculating the area of the minimum bounding rectangle, taking the square root of the area of the minimum bounding rectangle as the diameter of the hand in the fisting state, thus obtaining the area of the hand in the fisting state according to a circular area calculation formula, and obtaining reference region size information of the stereo reference object; according to the reference region size information of the stereo reference object and the actual size information of the stereo reference object, obtaining a second mapping ratio, and the specific process is as described in step S1302, which will not be described in detail here; according to the food image in the top image, since the to-be-estimated food region occupied by the food to be estimated is circular, acquiring the pixel area of the to-be-estimated food region to obtain the food region size information, so as to acquire the food size information according to the second mapping ratio and the food region size information, that is, the real area of the food to be estimated, the specific process is as described in step S1303 and step S1304, which will not be repeated here; based on the food image, the container shape of the food to be estimated is determined through a deep learning model, for example, the container shape is obtained as a dish, a bowl, etc.; obtaining the volume information of the food to be estimated according to the container shape and food size information, for example, detecting that the container shape is a dish, calculating the true diameter of the food to be estimated according to the real area of the food to be estimated, taking one tenth of the true diameter of the food to be estimated as the height value of the food to be estimated, and calculating the volume of the food to be estimated by a cylinder calculation formula, for example, detecting that the container shape is a bowl, since the shape of the bowl can be approximately seen as a hemisphere, the real radius of the food to be estimated may be calculated according to the real area of the food to be estimated, and then the volume information of the food to be estimated may be obtained according to the hemispherical volume calculation formula.

In the above embodiments, the calculation method of food volume uses the hand as the stereo reference object, which makes the application scenarios of the calculation method of food volume provided in at least one embodiment of the present disclosure wider. The food volume calculation can be completed only by hands, thereby making the method flexible and easy to operate. In addition, since the shape of the stereo reference object is approximately spherical, the calculation accuracy of the food volume will not be affected by the shooting direction, and the operation difficulty will be reduced.

The following describes in detail the hand detection model and the method for obtaining the fist region according to the hand detection model in the embodiments of the present disclosure, but the embodiments of the present disclosure are not limited to the following specific methods.

If the stereo reference image includes not only the hand in the fisting state, but also the arm part, it is necessary to acquire the fist image by hand detection model, extract the fist region in the fist image, and acquire the pixel area of the fist region. The implementation process of the hand detection model will be specifically explained by taking the stereo reference image including hand and arm as an example. It should be noted that the present disclosure is not limited to performing hand model detection on the stereo reference image, and can also obtain hand image from any to-be-processed image including hand image through the hand detection model, which is not limited by the present disclosure.

At present, the general images are based on RGB (Red, Green and Blue) color space, in which the skin color of human body images is greatly influenced by brightness, so it is difficult to separate skin color points from non-skin color points. That is to say, in face images processed in RGB color space, skin color points are discrete points with many non-skin color points embedded in the middle, which brings a problem of skin color region calibration (such as face calibration, eye calibration, etc.). YCrCb color space is often used in face detection, because the influence of brightness can be ignored when RGB color space is changed into YCrCb color space, and skin color will be clustered very well because YCrCb color space is less affected by brightness, so that three-dimensional color space can be mapped to two-dimensional CrCb plane, and skin color points can form a certain shape, so as to achieve the purpose of recognizing the human image according to skin color.

"Y" in YCrCb color space represents brightness, that is, gray scale value of pixels, while "Cr" and "Cb" represent chroma, which are used to describe the color and saturation of image and specify the color of pixels. "Cr" represents the difference between the red part of RGB input signal and RGB signal luminance value, that is, red chroma component of pixels, while "Cb" represents the difference between blue part of RGB input signal and RGB signal luminance value, that is, blue chroma component of pixels. The luminance value of RGB signal is obtained by superimposing specific parts of RGB input signal together. That is to say, YCrCb color space is a color model that separates brightness separately. Skin color points will not be affected by light brightness and will be easy to separate by using the color model.

For example, when the stereo reference image is processed by the hand detection model to obtain the fist image, first, the stereo reference image is mapped to the YCbCr color space to obtain the mapped image; then, projecting the mapped image on the CbCr plane to obtain a skin color sample image, and the skin color sample image comprises skin color sample points corresponding to pixels of the stereo reference image; and finally, traversing the skin color sample image, during the traversing process, if a skin color sample point is located within the ellipse boundary and the ellipse of a skin pixel, marking the pixel value of the pixel of the stereo reference image corresponding to skin color sample point as a second value (e.g. 0), if a skin color sample point is not located within the ellipse boundary and ellipse of a skin pixel, marking the pixel value of the pixel of the stereo reference image corresponding to skin color sample point as a first value (e.g. 255), so as to obtain a mask image corresponding to the stereo reference image, and the mask image is a fist image. For example, FIG. 4A is a schematic diagram of the fist image, in which the black region is the mask image corresponding to the arm and the hand in the fisting state.

For example, after obtaining the fist image, extracting the fist region includes the following operations. Firstly, taking the pixels whose gray scale values are the second value in the fist image as the hand region, for example, taking the pixels whose gray scale values are 0 gray scale in the fist image as the hand region, that is, the black region in FIG. 4A. Then, detecting the first side edge of the hand region in the column detection direction of the hand region, and calculating the slope between every M pixels on the first side edge of the hand region to obtain a plurality of slope values. Finally, according to the numerical relationship of the slope values, determining the positions of edge pixels of the fist region, and obtaining the fist region in the fist image.

For example, the column detection direction is toward the wrist, and the first side edge is the edge where the thumb of the hand is located. The number of slope values is N, and the m-th slope value corresponds to the pixel Dm+1 and pixel Dm. For example, after obtaining N slope values, the N slope values are sorted according to the column detection direction. If the (m+1)-th slope value is larger than the m-th slope value for the first time, the position of the pixel Dm+1 corresponding to both the m-th slope value and the (m+1)-th slope value is taken as the position of the edge pixel of the fist region, thus obtaining the fist region in the fist image according to the positions of the edge pixels.

Figure 4A:
FIG. 4A is a schematic diagram of a fist image provided by at least one embodiment of the present disclosure.
Figure 4B:
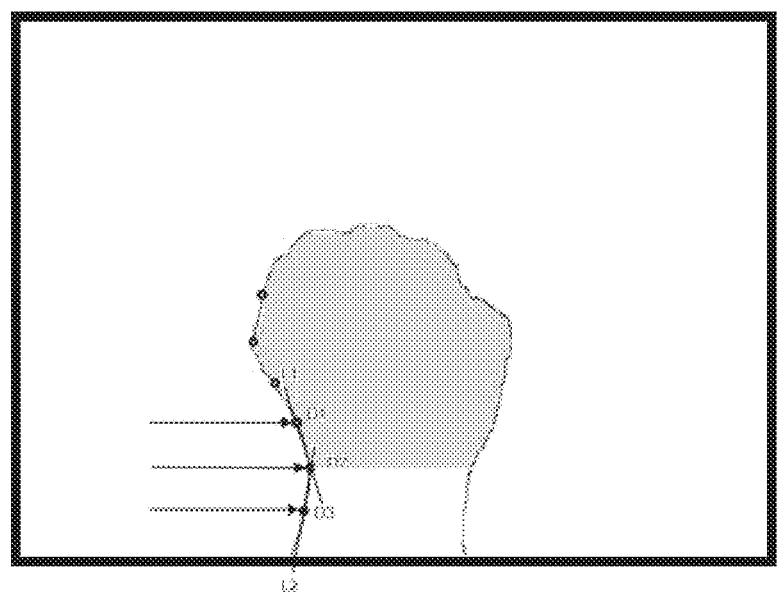
FIG. 4B is a schematic diagram of the process of extracting a fist region in the fist image shown in FIG. 4A provided by at least one embodiment of the present disclosure.

FIG. 4B is a schematic diagram of the process of extracting the fist region in the fist image shown in FIG. 4A provided by at least one embodiment of the present disclosure. In FIG. 4B, pixel D1, pixel D2 and pixel D3 represent three pixels to be processed in the fist image, straight line L1 is the connecting line between pixel D1 and pixel D2, and the slope of L1 is expressed as k1. The straight line L2 is the connecting line between pixel D2 and pixel D3, and the slope of L2 is expressed as k2. The shaded region in the figure represents the extracted fist region, and the fist image formed by black lines is the hand region.

As shown in FIG. 4B, the column detection direction is from top to bottom, and the first side edge is the left edge of the hand region in the figure. For the left edge of hand region, calculating the slope between every 10 pixels on the left edge to get a plurality of slope values, for example, calculating slope value k1 between pixel D1 and pixel D2, calculating slope value k2 between pixel D2 and pixel D3. If slope values are arranged in the column detection direction, and k2 is larger than k1 for the first time, pixel D2 will be the edge pixel of the fist region, thus obtaining the fist region shown by shading in FIG. 4B.

For example, when the image obtained by shooting food contains many kinds of foods, for example, containers contain their own foods, the regions of foods can be divided by techniques such as food recognition and image segmentation, and then the volume and heat of each food can be calculated separately.

At least one embodiment of the present disclosure also provides a calculating method of food calories, includes: acquiring a type of food to be estimated; acquiring volume information of the food to be estimated according to the above embodiments; determining a density of the food to be estimated according to the type of the food to be estimated, and obtaining a weight of the food to be estimated based on the density and the volume information of the food to be estimated; determining a heat density of the food to be estimated according to the type of the food to be estimated, and obtaining calories of the food to be estimated based on the heat density and the weight of the food to be estimated.

Figure 5A:
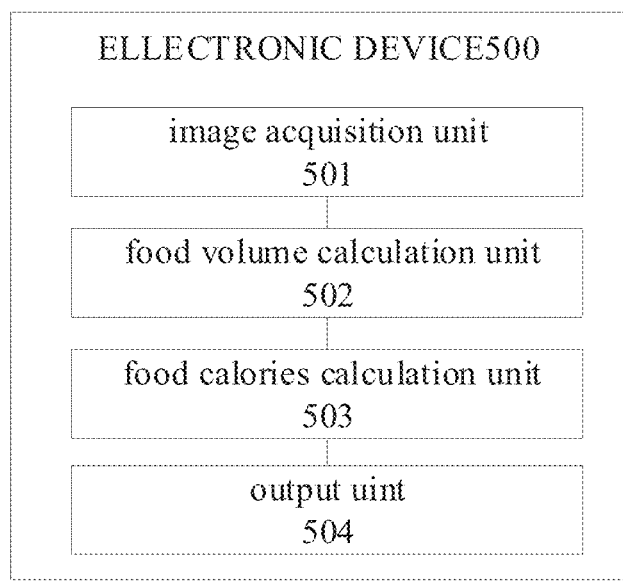
FIG. 5A is a schematic block diagram of an electronic apparatus provided by at least one embodiment of the present disclosure.

At least one embodiment of the present disclosure also provides an electronic device, and FIG. 5A is a schematic block diagram of an electronic device provided by at least one embodiment of the present disclosure.

The electronic device includes a food volume calculation unit configured to execute the calculation method of food volume provided by at least one embodiment of the present disclosure to obtain volume information of food to be estimated. The electronic device may further comprise a food calories calculation unit, the food calories calculation unit is configured to acquire the type of food to be estimated, determine the density of food to be estimated according to the type, obtain the weight of food to be estimated based on the density and volume information of food to be estimated, and then determine the heat density of the food to be estimated according to the type of the food to be estimated, thereby obtaining the calories of the food to be estimated according to the heat density of the food to be estimated and the weight of the food to be estimated. The electronic device can be implemented as a server or a terminal device in different examples.

For example, when the electronic device is implemented as a server, another terminal device (e.g., a mobile phone, etc.) communicating with the server through a communication network. For example, providing reference image(s) corresponding to the stereo reference object and food image(s) corresponding to the food to be estimated to the server, or receiving the volume information of food to be estimated calculated by the server through the food volume calculation unit, or further receiving the calories of food to be estimated from the server through the food calories calculation unit. Correspondingly, in order to communicate with other terminal devices, in addition to the above-mentioned food volume calculation unit and/or food calories calculation unit, the server may further include an image receiving unit to receive reference image(s) corresponding to the stereo reference object and food image(s) corresponding to the food to be estimated from the communicating terminal device, and a calculation result output unit to output the calculated volume information and/or calories of the food to be estimated to the communicating terminal device. For example, other terminal devices shoot reference image(s) corresponding to the stereo reference object and food image(s) corresponding to the food to be estimated through their own image acquisition unit (such as camera), or after obtaining the aforementioned calculation result(s), other terminal devices provide the calculation result(s) to users in the ways of display, voice, printing, etc. For example, when the electronic device is implemented as a terminal, as shown in the FIG. 5A, the electronic device 500 includes an image acquisition unit 501, a food volume calculation unit 502, a food calories calculation unit 503 and an output unit 504. For example, the electronic device 500 can be a mobile terminal, which can be a mobile phone, a tablet computer, a smart watch and other device.

The image acquisition unit 501 is configured to acquire a reference image corresponding to the stereo reference object and a food image corresponding to the food to be estimated. For example, the image acquisition unit 501 is a camera of a mobile terminal, and the reference image and food image in the calculation method of food volume can be acquired by the camera of the mobile terminal.

The food volume calculation unit 502 is configured to execute the calculation method of food volume provided by at least one embodiment of the present disclosure to obtain the volume information of the food to be estimated.

The food calories calculation unit 503 is configured to acquire the type of the food to be estimated, determine the density of the food to be estimated according to the type of the food to be estimated, and obtain the weight of the food to be estimated based on the density and volume information of the food to be estimated; determine the heat density of the food to be estimated according to the type of the food to be estimated, and obtain the calories of the food to be estimated based on the heat density and the weight of the food to be estimated.

The output unit 504 is configured to display or output volume information and/or calories information of the food to be estimated. For example, the output unit can be a display screen, a microphone, a printout unit, etc., which provides the volume information and/or calories information of the food to be estimated to the user in the form of display, voice or printing, or the output unit can output the volume information and/or calories information of the food to be estimated to other terminals for display or printing, etc.

The above-mentioned food volume calculation unit, food calories calculation unit, image receiving unit, calculation result output unit, etc. can be realized by hardware, software, firmware or any combination of the three.

FIG. 5B to FIG. 5F show product interface diagrams using the calculation method of food volume and calculation method of food calories provided by at least one embodiment of the present disclosure. For example, the calculation method of food volume and calculation method of food calories provided by at least one embodiment of the present disclosure are applied to an electronic device 500. For example, the electronic device 500 is a server, and the product interface diagram is an interface diagram of terminal equipment used in cooperation with the electronic device 500, such as mobile phone, tablet computer, smart watch and other equipment.

For example, the reference image corresponding to the stereo reference object and food image corresponding to the food to be estimated are shot by the camera of the terminal equipment, and the terminal equipment sends the reference image and food image to the image receiving unit of the server through the communication network. The server calculates the food volume and food calories through the food volume calculation unit and the food calories calculation unit according to the received food image and reference image, and finally sends the calculation results to the terminal equipment through the calculation result output unit for display.

Figure 5B:
FIG. 5B to FIG. 5F are product interface diagrams for implementing the calculation method of food volume and the calculation method of food calories provided by at least one embodiment of the present disclosure.

FIG. 5B is the main interface diagram of the terminal device. As shown in the figure, by clicking the "AI recognition" button in the middle of the menu bar, reference images and food images can be taken, so that the volume of food to be estimated and the calories of food to be estimated can be calculated according to the aforementioned embodiment. By clicking the "Mine" button in the lower right corner of the menu bar, the size information of the user's hand in the fisting state can be input, and the size information will be stored in the personal database.

Figure 5C:
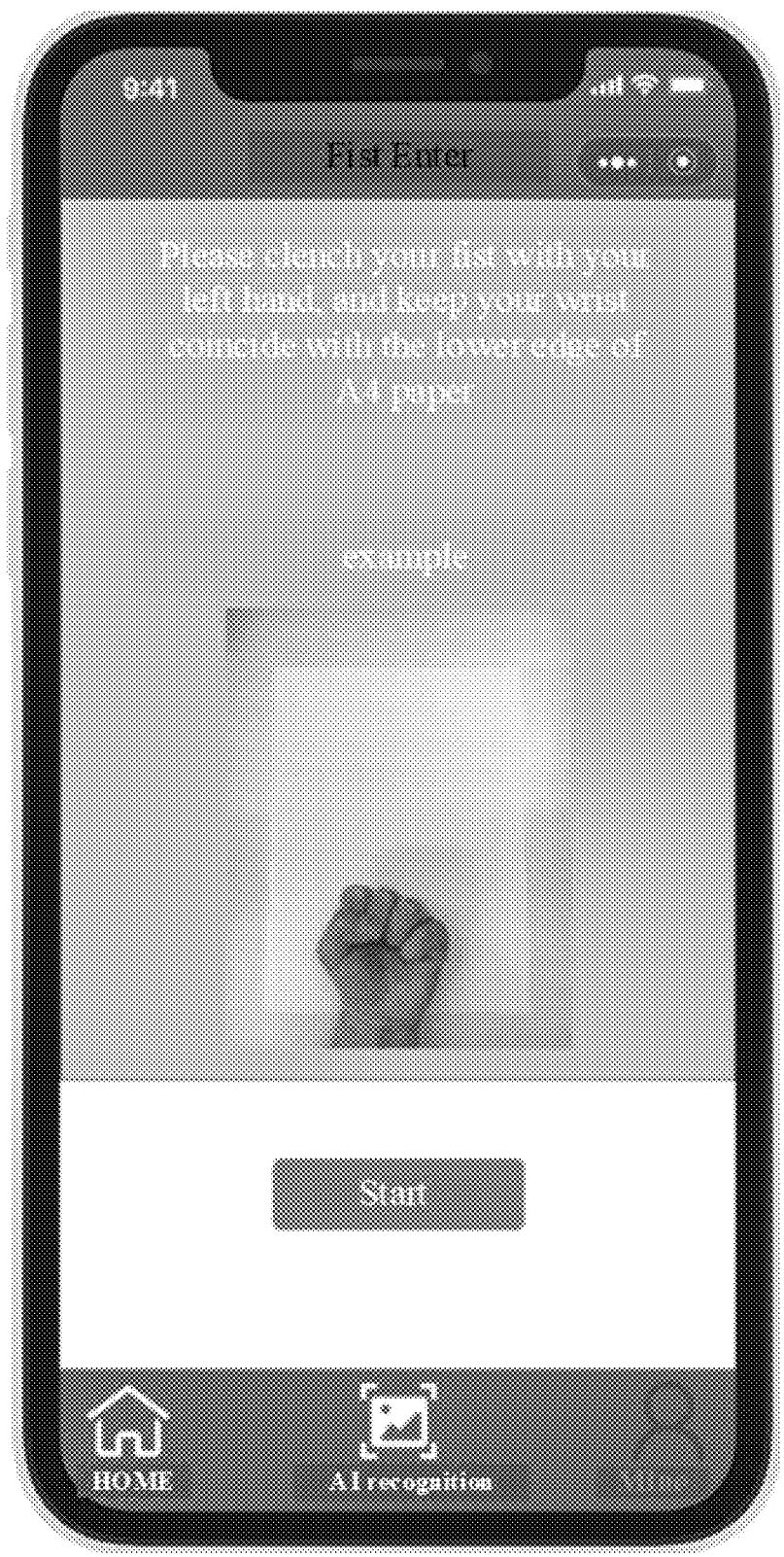

For example, when entering the size information of the hand in the fisting state of the user, as shown in FIG. 5C, the user enters the image of the hand in the fisting state that is taken in front of the A4 paper according to the prompt, and the wrist is at the lower edge of A4 paper, thus obtaining the actual size information of the hand in the fisting state.

Figure 5D:
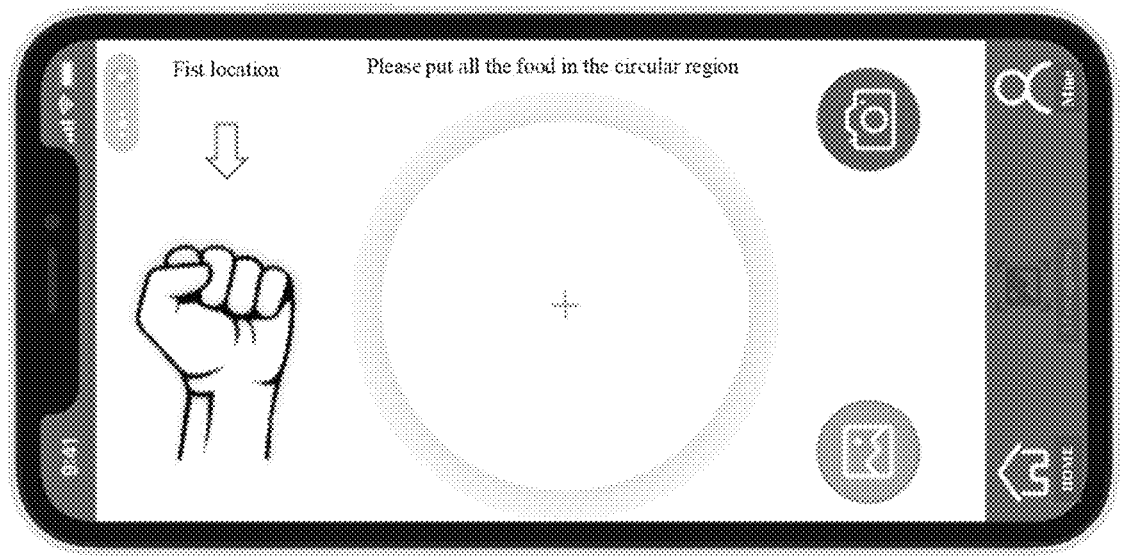
Figure 5E:
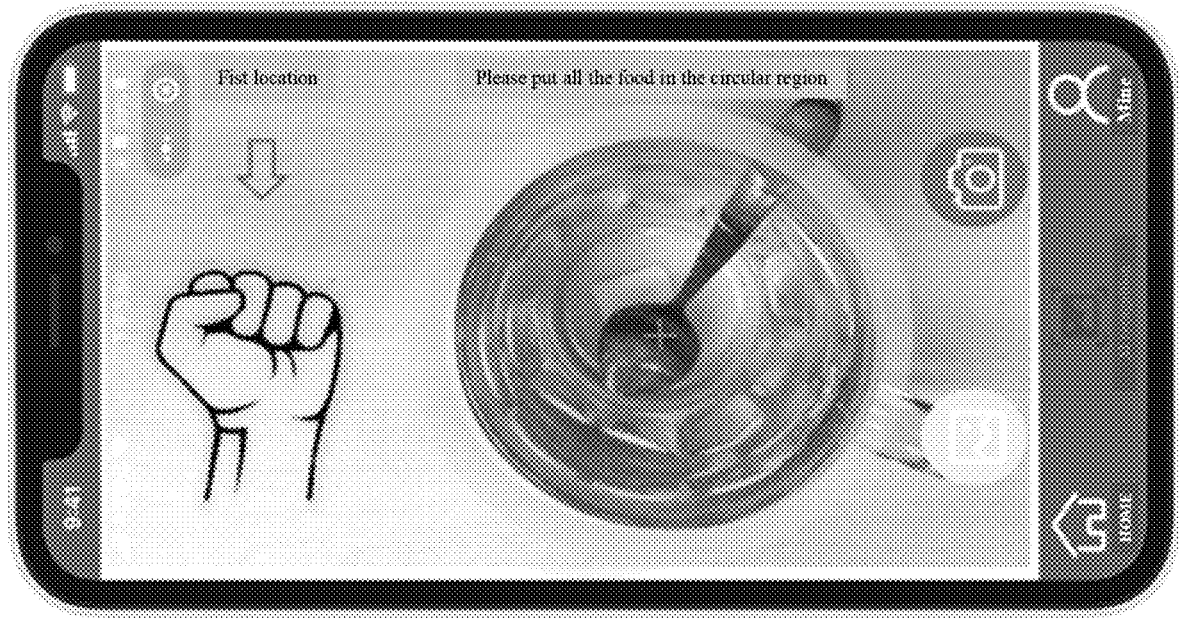

For example, when acquiring the volume and calories of food to be estimated, after clicking the "AI recognition" button, as shown in FIG. 5D and FIG. 5E, according to the prompt, shooting an image including the hand in the fisting state and the food to be estimated to obtain a reference image and a food image. Then, the terminal equipment uploads the reference image and the food image to the server to calculate the volume and calories of food to be estimated, and obtains the volume and food to be estimated through the calculation result output unit of the server.

Figure 5F:
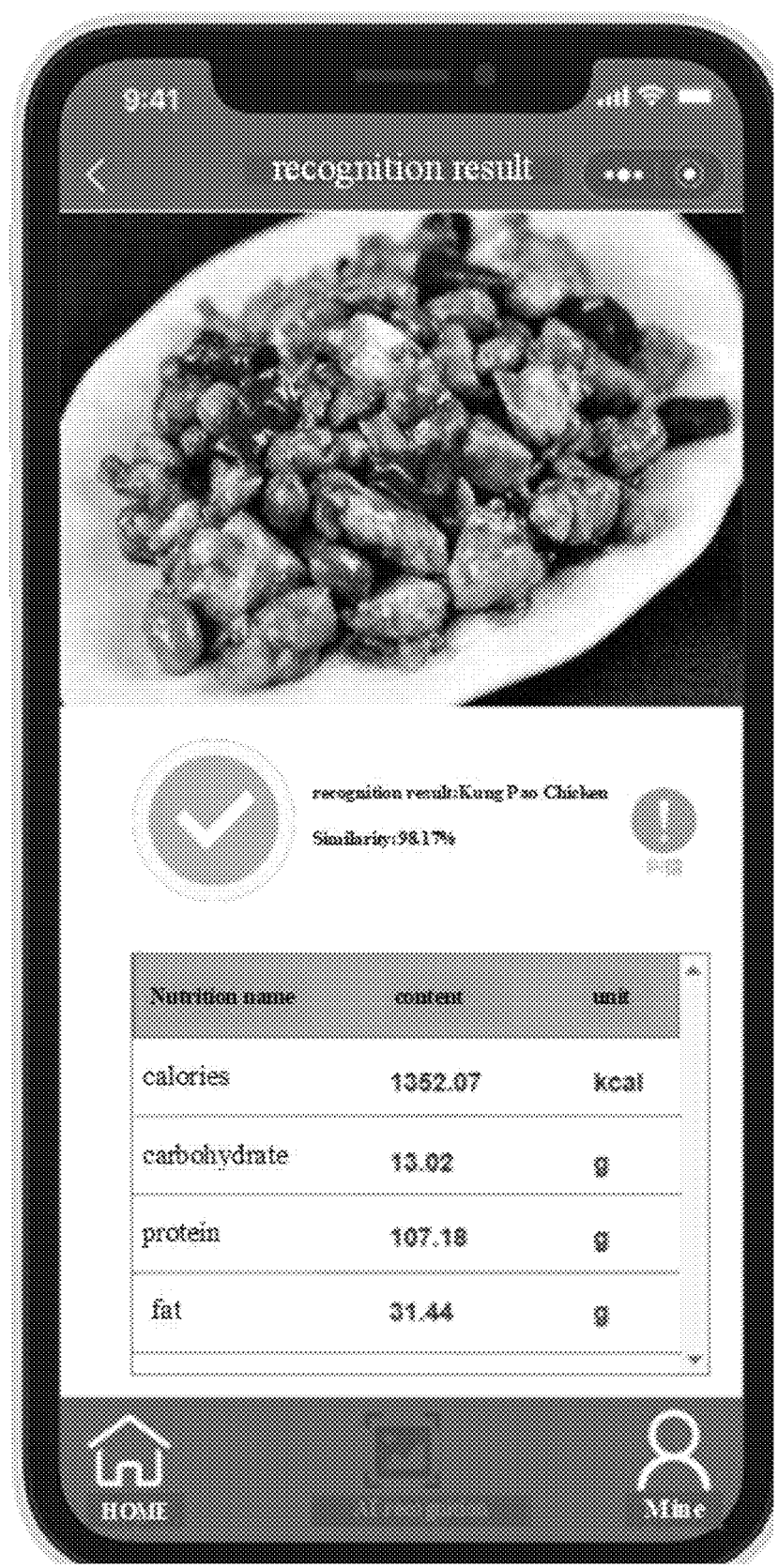

After obtaining the volume and calories of the food to be estimated, as shown in FIG. 5F, the mobile terminal displays the calculation results of the server, and the calculation results include the name of the food to be estimated, the calories of the food to be estimated and other information.

For example, the calculation process of the volume of food to be estimated and the calories of food to be estimated can also be realized in a mobile terminal (without a server). Or, a part of the calculation process is set at the mobile terminal, and the other part of the calculation process is executed at the server.

Figure 6:
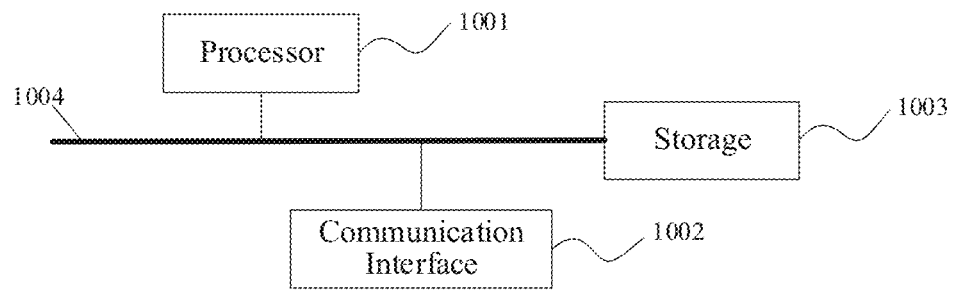
FIG. 6 is a schematic block diagram of an electronic device provided by at least one embodiment of the present disclosure.

At least one embodiment of the present disclosure further provides an electronic device. FIG. 6 is a schematic block diagram of the electronic device provided by at least one embodiment of the present disclosure.

For example, as shown in FIG. 6, the electronic device includes a processor 1001, a communication interface 1002, a memory 1003 and a communication bus 1004. The processor 1001, the communication interface 1002, and the memory 1003 communicate with each other through the communication bus 1004, and the components such as the processor 1001, the communication interface 1002, and the memory 1003 may also communicate with each other through a network connection. The present disclosure does not limit the type and function of the network.

For example, in at least one example, the electronic device further includes an image acquisition device such as at least one camera, thereby acquiring various required images.

For example, the memory 1003 may store computer executable instructions non-transiently. When the processor 1001 is used to execute computer executable instructions, the computer executable instructions are executed by the processor 1001 to implement the calculation method of food volume according to any of the above embodiments. For the specific implementation of each step of the calculation method of food volume and related explanations, please refer to the above embodiments of the calculation method of food volume, which will not be repeated here.

For example, the processor 1001 runs the program stored in the memory 1003 to realize the implementation of the calculation method of food volume, which is the same as the implementation mentioned in the above embodiments of the calculation method of food volume mentioned, which will not be repeated here.

For example, the communication bus 1004 may be a peripheral component interconnect standard (PCI) bus or an extended industry standard architecture (EISA) bus, etc. The communication bus 1004 may be divided into address bus, data bus, control bus and so on. For convenience of presentation, only one thick line is used in the drawing, which does not mean that there is only one bus or one type of bus.

For example, the communication interface 1002 is used to realize communication between the electronic device and other devices.

For example, the processor 1001 and the memory 1003 may be disposed on the server side (or on the cloud).

For example, the processor 1001 may control other components in the electronic device to perform desired functions. The processor 1001 may be a central processing unit (CPU), a network processor (NP), etc., and may also be a digital signal processor (DSP), an application specific integrated circuit (ASIC), a field programmable gate array (FPGA) or other programmable logic devices, discrete gate or transistor logic devices, and discrete hardware components. A central processing unit (CPU) may be X86 or ARM architecture.

For example, the memory 1003 may include any combination of one or more computer program products, which may include various forms of computer-readable storage media, such as volatile memory and/or nonvolatile memory. The volatile memory may include random access memory (RAM) and/or cache, for example. The nonvolatile memory may include, for example, read-only memory (ROM), hard disk, erasable programmable read-only memory (EPROM), portable compact disk read-only memory (CD-ROM), USB memory, flash memory, and the like. One or more computer executable instructions may be stored on the computer-readable storage medium, and the processor 1001 may execute the computer-executable instructions to realize various functions of the electronic device. Various applications and various data can also be stored in the storage medium.

For example, the electronic device may be a server, which transmits the food volume obtained by the calculation method of food volume provided by at least one embodiment of the present disclosure and the food calories obtained by the calculation method of food calories provided by at least one embodiment of the present disclosure to the terminal device for display.

For example, the server receives information such as pictures sent by the terminal device, implements the calculation process of food volume, and sends calculation result to the terminal device for display.

For example, the detailed description of the calculation process of the food volume by electronic device can refer to the relevant description in the embodiments of the calculation method of food volume, which will not be repeated here.

Figure 7:
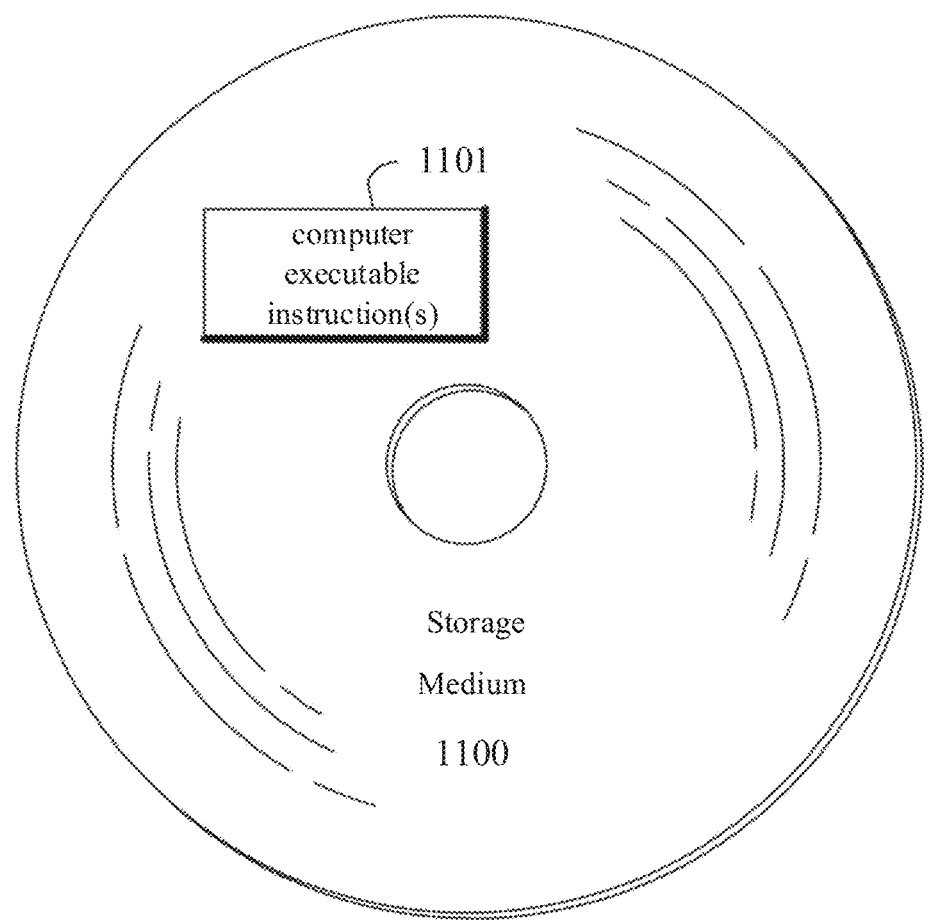
FIG. 7 is a schematic diagram of a storage medium provided by at least one embodiment of the present disclosure.

FIG. 7 is a schematic diagram of a computer readable storage medium provided by at least one embodiment of the present disclosure. For example, as shown in FIG. 7, one or more computer executable instructions 1101 may be stored on a storage medium 1100 non-temporarily. For example, when the computer executable instructions 1101 are executed by a processor, one or more steps in the calculation method of food volume described above may be performed.

For example, the storage medium 1100 can be applied to the above-mentioned electronic device and/or food volume calculation device 1400. For example, the storage medium 1100 may include a memory 1003 in the electronic device.

For example, for the description of the storage medium 1100, reference can be made to the description of the memory in the embodiment of electronic device, which will not be repeated here.

Figure 8:
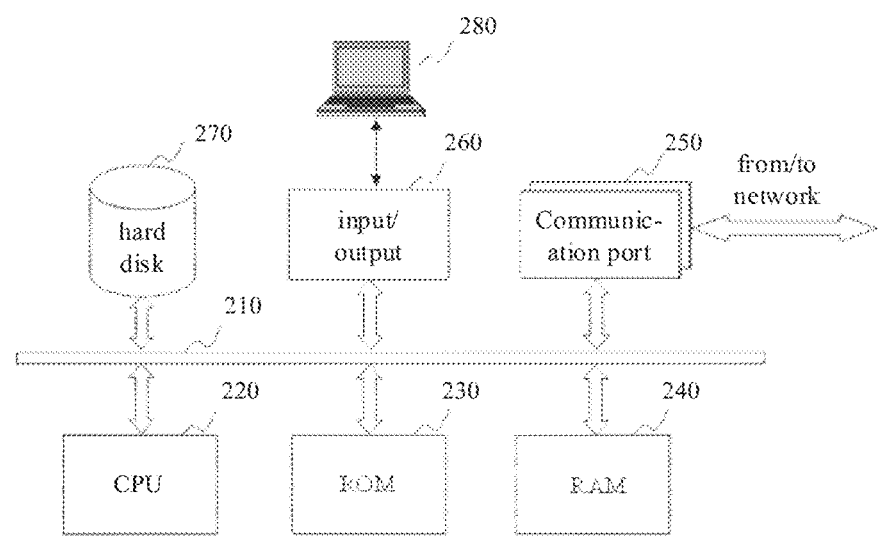
FIG. 8 is a schematic diagram of a hardware environment provided by at least one embodiment of the present disclosure.

FIG. 8 is a schematic diagram of a hardware environment provided by at least one embodiment of the present disclosure. The electronic device provided by the present disclosure can be applied to the Internet system.

The functions of the food volume calculation device and/or electronic device involved in the present disclosure can be realized by using the computer system provided in FIG. 8. Such computer systems can include personal computers, notebook computers, tablet computers, mobile phones, personal digital assistants, smart glasses, smart watches, smart rings, smart helmets and any smart portable devices or wearable devices. The specific system in this embodiment uses the functional block diagram to explain a hardware platform including a user interface. This kind of computer equipment can be a general purpose computer equipment or a special purpose computer equipment. Both kinds of computer equipment can be used to realize the food volume calculation device and/or electronic device in this embodiment. A computer system may include any component that implements the information required to implement the calculation of food volume as currently described. For example, a computer system can be implemented by a computer device through its hardware devices, software programs, firmware, and combinations thereof. For convenience, only one computer device is drawn in FIG. 8, but the computer functions related to the information that is needed to calculate the food volume described in this embodiment can be implemented by a group of similar platforms in a distributed manner, which disperses the processing load of the computer system.

As shown in FIG. 8, the computer system can include a communication port 250, which is connected with a network for realizing data communication. For example, the computer system can send and receive information and data through the communication port 250, which is, the communication port 250 can realize wireless or wired communication between the computer system and other electronic devices to exchange data. The computer system may also include a processor group 220 (i.e., the processor described above) for executing program instructions. The processor group 220 may be composed of at least one processor (e.g., CPU). The computer system may include an internal communication bus 210. A computer system may include different forms of program storage units and data storage units (i.e., the memory or storage medium described above), such as a hard disk 270, a read-only memory (ROM) 230, and a random access memory (RAM) 240, which can be used to store various data files used for computer processing and/or communication, and possible program instructions executed by the processor group 220. The computer system may also include an input/output component 260, which is used to realize the input/output data flow between the computer system and other components (e.g., user interface 280, etc.).

Generally, the following devices can be connected to the input/output component 260: input devices, for example, touch screens, touch pads, keyboards, mice, cameras, microphones, accelerometers, gyroscopes, etc.; output devices, for example, a liquid crystal display (LCD), a speaker, a vibrator, and the like; storage devices, for example, magnetic tapes, hard disks, etc.; and communication interface.

Although FIG. 8 shows a computer system with various devices, it should be understood that the computer system is not required to be provided with all the devices shown, and instead, the computer system may be provided with more or less devices.

For this disclosure, the following points need to be explained:

(1) The drawings of the embodiments of this disclosure only refer to the structures related to the embodiments of this disclosure, and other structures can refer to general designs.

(2) In the drawings for describing embodiments of the present disclosure, the thickness and size of layers or structures are exaggerated for clarity. It can be understood that when an element such as a layer, film, region or substrate is said to be located "above" or "below" another element, the element may be "directly" located "above" or "below" another element, or there may be intermediate elements.

(3) The embodiments of the present disclosure and the features in the embodiments can be combined with each other to obtain new embodiments without conflict.

The above is only the specific embodiment of this disclosure, but the protection scope of this disclosure is not limited to this. Any person familiar with the technical field can easily think of changes or substitutions within the technical scope disclosed in this disclosure, which should be covered within the protection scope of this disclosure. Therefore, the protection scope of this disclosure shall be subject to the protection scope of the claims.

What is claimed is:

1. A calculation method of food volume, comprising:
acquiring actual size information of a stereo reference object;
acquiring a reference image corresponding to the stereo reference object and a food image corresponding to food to be estimated; and
acquiring volume information of the food to be estimated, according to the actual size information of the stereo reference object, reference region size information acquired based on the reference image, and food region size information acquired based on the food image, wherein the acquiring the reference image corresponding to the stereo reference object and the food image corresponding to food to be estimated, comprises:
acquiring one reference image corresponding to the stereo reference object and one food image corresponding to the food to be estimated in a same image-shooting mode, wherein the volume information of the food to be estimated is acquired, according to the actual size information of the stereo reference object, the reference region size information acquired based on the one reference image, and the food region size information acquired based on the one food image; or
acquiring a plurality of reference images and a plurality of food images which are correspondingly acquired in pair corresponding to the stereo reference object and the food to be estimated in a plurality of image-shooting modes, wherein the volume information of the food to be estimated is acquired, according to the actual size information of the stereo reference object, the reference region size information acquired based on the plurality of reference images, and the food region size information acquired based on the plurality of food images,
wherein the same image-shooting mode or each of the plurality of image-shooting modes at least comprises a shooting distance and a shooting direction, wherein the plurality of image-shooting modes comprise a first image-shooting mode and a second image-shooting mode, a shooting direction of the first image-shooting mode and a shooting direction of the second image-shooting mode cross each other,
the plurality of reference images comprise a first reference image obtained in the first image-shooting mode and a second reference image obtained in the second image-shooting mode, and
the plurality of food images comprise a first food image obtained in the first image-shooting mode and a second food image obtained in the second image-shooting mode.

2. The method according to claim 1, wherein the reference image and the food image acquired in pair in the same image-shooting mode are a pair of images corresponding to each other, or the reference image and the food image acquired in pair in the same image-shooting mode belong to a same image.

3. The method according to claim 1, wherein the acquiring the actual size information of the stereo reference object comprises:
acquiring a stereo reference image in which the stereo reference object is placed on one side of a second reference object with a reference area that is acquirable; and
acquiring the actual size information of the stereo reference object according to the stereo reference image and the reference area, wherein the stereo reference image comprises information for calculating the reference area of the second reference object.

4. The method according to claim 1, wherein the acquiring the actual size information of the stereo reference object according to the stereo reference image and the reference area comprises:
acquiring a pixel area of the second reference object in the stereo reference image;
obtaining a first mapping ratio based on the pixel area of the second reference object and the reference area;
acquiring a pixel area of a region occupied by the stereo reference object in the stereo reference image; and
acquiring a volume of the stereo reference object according to the first mapping ratio and the pixel area of the region occupied by the stereo reference object, to obtain the actual size information of the stereo reference object.

5. The method according to claim 4, wherein pixel values of pixels corresponding to the second reference object in the stereo reference image are within a first value range, the acquiring the pixel area of the region occupied by the stereo reference object in the stereo reference image comprises:
taking pixels in the stereo reference image whose pixel values do not meet the first value range as a region occupied by the stereo reference object, to obtain the pixel area of the region occupied by the stereo reference object; or,
obtaining the pixel area of the region occupied by the stereo reference object according to a region occupied by the stereo reference object acquired through a deep learning model.

6. The method according to claim 4, wherein the acquiring the pixel area of the second reference object in the stereo reference image comprises:
acquiring a minimum bounding rectangle of the second reference object in the stereo reference image and a pixel area of the minimum bounding rectangle, and taking the pixel area of the minimum bounding rectangle as the pixel area of the second reference object, wherein pixel values of pixels corresponding to the second reference object in the stereo reference image are within a first value range, and the minimum bounding rectangle of the second reference object is obtained according to positions of the pixels whose pixel values are within the first value range, and
the acquiring the pixel area of the region occupied by the stereo reference object in the stereo reference image comprises:
taking pixels in the minimum bounding rectangle whose pixel values do not meet the first value range as the region occupied by the stereo reference object, to obtain the pixel area of the region occupied by the stereo reference object.

7. The method according to claim 4, wherein the stereo reference object comprises a hand in a fisting state and is processed in a spherical manner, the acquiring the pixel area of the region occupied by the stereo reference object in the stereo reference image comprises:
in response to that a wrist part of the hand in the stereo reference image is not at an edge of the second reference object, acquiring a first image according to a hand detection model, extracting a first region of the first image, and acquiring a pixel area of the first region as the pixel area of the region occupied by the stereo reference object; or
in response to that the wrist part of the hand in the stereo reference image is at the edge of the second reference object, taking pixels in the stereo reference image whose pixel values do not meet a first value range as the first region, and obtaining the pixel area of the first region as the pixel area of the region occupied by the stereo reference object.

8. The method according to claim 1, wherein the acquiring the volume information of the food to be estimated, according to the actual size information of the stereo reference object, the reference region size information acquired based on the plurality of reference images, and the food region size information acquired based on the plurality of food images, comprises:

for each reference image of the plurality of reference images, acquiring a pixel area of a region occupied by the stereo reference object in the reference image, to obtain the reference region size information of the stereo reference object;

acquiring a second mapping ratio, according to the reference region size information of the stereo reference object and the actual size information of the stereo reference object;

extracting a to-be-estimated food region occupied by the food to be estimated in the first food image, to obtain the food region size information;

acquiring food size information according to the food region size information and the second mapping ratio;

extracting to-be-estimated food regions occupied by the food to be estimated in the plurality of food images, respectively, and determining a container shape of the food to be estimated according to the to-be-estimated food regions; and acquiring the volume information of the food to be estimated according to the container shape of the food to be estimated and the food size information.

9. The method according to claim 8, wherein the acquiring the volume information of the food to be estimated, according to the actual size information of the stereo reference object, the reference region size information, and the food region size information, further comprises:

extracting the to-be-estimated food region occupied by the food to be estimated in the second food image, and determining a height value of the food to be estimated according to the to-be-estimated food region and the second mapping ratio; and acquiring the volume information of the food to be estimated according to the container shape of the food to be estimated, the height value of the food to be estimated, and the food size information.

10. The method according to claim 3, wherein the food to be estimated is placed in a container, a shape of the container is known and acquirable, or the shape of the container is determined according to the one food image, the acquiring the volume information of the food to be estimated, according to the actual size information of the stereo reference object, the reference region size information acquired based on the one reference image, and the food region size information acquired based on the one food image, comprises:

acquiring a pixel area of a region occupied by the stereo reference object in the one reference image, to obtain the reference region size information of the stereo reference object;

obtaining a second mapping ratio according to the reference region size information of the stereo reference object and the actual size information of the stereo reference object;

extracting a to-be-estimated food region occupied by the food to be estimated in the one food image, to obtain the food region size information;

obtaining food size information according to the food region size information and the second mapping ratio; and obtaining the volume information of the food to be estimated according to the shape of the container and the food size information.

11. The method according to claim 8, wherein, for an image to be processed including the food to be estimated, the extracting the to-be-estimated food region occupied by the food to be estimated comprises:

dividing the image to be processed into a plurality of region sets, and performing a similarity calculation on each region set of the plurality of region sets, to obtain a similarity value of each region set;

merging region sets with similarity values meeting a preset threshold to obtain a plurality of merged regions; and taking a closed region out of the plurality of merged regions with a largest pixel area as the to-be-estimated food region of the image to be processed, wherein the similarity calculation comprises one or more combinations of color similarity calculation, texture similarity calculation, size similarity calculation, and overlap similarity calculation.

12. The method according to claim 8, wherein, for an image to be processed including the food to be estimated, the extracting the to-be-estimated food region occupied by the food to be estimated comprises:

performing edge recognition on the image to be processed based on a depth convolution network model, to obtain the to-be-estimated food region of the food to be estimated in the image to be processed.

13. A calculation method of food calories, comprising:

acquiring a type of food to be estimated;

acquiring volume information of the food to be estimated according to the calculation method of food volume according to claim 3;

determining a density of the food to be estimated according to the type of the food to be estimated, and obtaining a weight of the food to be estimated based on the density and the volume information of the food to be estimated; and determining a heat density of the food to be estimated according to the type of the food to be estimated, and obtaining calories of the food to be estimated based on the heat density and the weight of the food to be estimated.

14. An electronic apparatus, comprising:

a food volume calculation unit, configured to perform a calculation method of food volume to obtain volume information of food to be estimated, wherein the calculation method of food volume comprises:

acquiring actual size information of a stereo reference object;

acquiring a reference image corresponding to the stereo reference object and a food image corresponding to the food to be estimated; and acquiring the volume information of the food to be estimated, according to the actual size information of the stereo reference object, reference region size information acquired based on the reference image, and food region size information acquired based on the food image, wherein the acquiring the reference image corresponding to the stereo reference object and the food image corresponding to food to be estimated comprises:

acquiring one reference image corresponding to the stereo reference object and one food image corresponding to the food to be estimated in a same image-shooting mode, wherein the volume information of the food to be estimated is acquired, according to the actual size information of the stereo reference object, the reference region size information acquired based on the one reference image, and the food region size information acquired based on the one food image; or acquiring a plurality of reference images and a plurality of food images which are correspondingly acquired in pair corresponding to the stereo reference object and the food to be estimated in a plurality of image-shooting modes, wherein the volume information of the food to be estimated is acquired, according to the actual size information of the stereo reference object, the reference region size information acquired based on the plurality of reference images, and the food region size information acquired based on the plurality of food images, wherein the same image-shooting mode or each of the plurality of image-shooting modes at least comprises a shooting distance and a shooting direction, wherein the plurality of image-shooting modes comprise a first image-shooting mode and a second image-shooting mode, a shooting direction of the first image-shooting mode and a shooting direction of the second image-shooting mode cross each other, the plurality of reference images comprise a first reference image obtained in the first image-shooting mode and a second reference image obtained in the second image-shooting mode, and the plurality of food images comprise a first food image obtained in the first image-shooting mode and a second food image obtained in the second image-shooting mode.

15. The electronic apparatus according to claim 14, further comprising a food calories calculation unit, configured to:

acquire a type of food to be estimated;

determine a density of the food to be estimated according to the type of the food to be estimated, and obtaining a weight of the food to be estimated based on the density and the volume information of the food to be estimated; and determine a heat density of the food to be estimated according to the type of the food to be estimated, and obtaining calories of the food to be estimated based on the heat density and the weight of the food to be estimated.

16. The electronic apparatus according to claim 15, further comprising:

an image acquisition unit, configured to acquire the reference image corresponding to the stereo reference object and the food image corresponding to the food to be estimated; and an output unit, configured to display or output the volume information and/or the calories of the food to be estimated.

17. An electronic device, comprising:

a storage, configured to non-instantaneously store computer executable instructions, and a processor, configured to execute the computer executable instructions, wherein, when the computer executable instructions are executed by the processor, a calculation method of food volume is achieved, wherein the calculation method of food volume comprises:

acquiring actual size information of a stereo reference object;

acquiring a reference image corresponding to the stereo reference object and a food image corresponding to food to be estimated; and acquiring volume information of the food to be estimated, according to the actual size information of the stereo reference object, reference region size information acquired based on the reference image, and food region size information acquired based on the food image, wherein the acquiring the reference image corresponding to the stereo reference object and the food image corresponding to food to be estimated comprises:

acquiring one reference image corresponding to the stereo reference object and one food image corresponding to the food to be estimated in a same image-shooting mode, wherein the volume information of the food to be estimated is acquired, according to the actual size information of the stereo reference object, the reference region size information acquired based on the one reference image, and the food region size information acquired based on the one food image; or acquiring a plurality of reference images and a plurality of food images which are correspondingly acquired in pair corresponding to the stereo reference object and the food to be estimated in a plurality of image-shooting modes, wherein the volume information of the food to be estimated is acquired, according to the actual size information of the stereo reference object, the reference region size information acquired based on the plurality of reference images, and the food region size information acquired based on the plurality of food images, wherein the same image-shooting mode or each of the plurality of image-shooting modes at least comprises a shooting distance and a shooting direction, wherein the plurality of image-shooting modes comprise a first image-shooting mode and a second image-shooting mode, a shooting direction of the first image-shooting mode and a shooting direction of the second image-shooting mode cross each other, the plurality of reference images comprise a first reference image obtained in the first image-shooting mode and a second reference image obtained in the second image-shooting mode, and the plurality of food images comprise a first food image obtained in the first image-shooting mode and a second food image obtained in the second image-shooting mode.

18. A non-transitory computer-readable storage medium, on which computer executable instructions are stored, wherein when the computer executable instructions are executed by a processor, the calculation method of food volume according to claim 3 is achieved.

* * * * *